US008389726B2

(12) United States Patent  
Piccariello

(10) Patent No.: US 8,389,726 B2
(45) Date of Patent: Mar. 5, 2013

(54) METAL COORDINATED COMPOSITIONS

(75) Inventor: Thomas Piccariello, Blacksburg, VA (US)

(73) Assignee: Synthonics, Inc., Blacksburg, VA (US)

( * ) Notice: Subject to any disclaimer, the term of this patent is extended or adjusted under 35 U.S.C. 154(b) by 0 days.

(21) Appl. No.: 13/183,972

(22) Filed: Jul. 15, 2011

(65) Prior Publication Data

US 2011/0275792 A1  Nov. 10, 2011

Related U.S. Application Data

(63) Continuation of application No. 12/317,931, filed on Dec. 30, 2008, now Pat. No. 7,989,440, which is a continuation of application No. 11/257,504, filed on Oct. 24, 2005, now abandoned.

(60) Provisional application No. 60/621,747, filed on Oct. 25, 2004.

(51) Int. Cl.
C07F 15/00  (2006.01)
C07F 7/00   (2006.01)
C07F 5/00   (2006.01)

(52) U.S. Cl. ............................................. 546/2; 546/10
(58) Field of Classification Search .................. 546/2, 10
See application file for complete search history.

(56) References Cited

U.S. PATENT DOCUMENTS

| | | | |
|---|---|---|---|
| 4,035,360 A | 7/1977 | Johnson et al. |
| 4,678,614 A | 7/1987 | Kamienski et al. |
| 5,002,689 A | 3/1991 | Mehta et al. |
| 5,043,168 A | 8/1991 | Patel et al. |
| 5,073,630 A | 12/1991 | Nunes et al. |
| 5,108,972 A | 4/1992 | Wang et al. |
| 5,186,923 A | 2/1993 | Piwnica-Worms et al. |
| RE34,222 E | 4/1993 | Bloch |
| 5,277,897 A | 1/1994 | Piwnica-Worms et al. |
| 5,324,637 A | 6/1994 | Thompson et al. |
| 5,346,670 A | 9/1994 | Renzoni et al. |
| 5,422,125 A | 6/1995 | Skyler et al. |
| 5,494,682 A | 2/1996 | Cohen et al. |
| 5,494,793 A | 2/1996 | Schindele et al. |
| 5,538,959 A | 7/1996 | Mauskop |
| 5,582,839 A | 12/1996 | McCarty |
| 5,637,745 A | 6/1997 | Silverman et al. |
| 5,684,149 A | 11/1997 | Morrow |
| 5,776,498 A | 7/1998 | McCarty |
| 5,776,504 A | 7/1998 | McCarty |
| 5,786,392 A | 7/1998 | Silverman et al. |
| 5,849,337 A | 12/1998 | Dixon |
| 5,871,769 A | 2/1999 | Fleming et al. |
| 5,876,757 A | 3/1999 | McCarty |
| 5,972,868 A | 10/1999 | Athey et al. |
| 6,054,434 A | 4/2000 | Kropp et al. |
| 6,063,637 A | 5/2000 | Arnold et al. |
| 6,090,411 A | 7/2000 | Pillay et al. |
| 6,100,297 A | 8/2000 | Weglicki |
| 6,124,464 A | 9/2000 | Hogberg et al. |
| 6,129,924 A | 10/2000 | Maurel et al. |
| 6,248,368 B1 | 6/2001 | Valletta |
| 6,316,652 B1 | 11/2001 | Steliou |
| 6,339,063 B1 | 1/2002 | Kropp et al. |
| 6,376,549 B1 | 4/2002 | Fine et al. |
| 6,380,234 B1 | 4/2002 | Makino et al. |
| 6,403,616 B1 | 6/2002 | Erickson et al. |
| 6,413,952 B1 | 7/2002 | Luengo et al. |
| 6,417,196 B1 | 7/2002 | Daniel et al. |
| 6,498,247 B2 | 12/2002 | Evans et al. |
| 6,589,564 B2 | 7/2003 | Valletta |
| 7,989,440 B2 | 8/2011 | Piccariello |

FOREIGN PATENT DOCUMENTS

| | | |
|---|---|---|
| EP | 1 011 664 | 11/2004 |
| EP | 1 510 214 | 3/2005 |
| EP | 1 011 689 | 1/2007 |
| JP | 09-227472 | 9/1997 |
| WO | WO 03/051300 A2 * | 6/2003 |

OTHER PUBLICATIONS

Moustafa, Azza A.M., Journal of Pharmaceutical and Biomedical Analysis, vol. 22, No. 1, pp. 45-58 (2000).*
Patel et al., Pharmaceutical Chemistry Journal, vol. 42, No. 12, pp. 687-692 (2008).*
Sultana et al., Medicinal Chemistry Journal, published online Jun. 16, 2012.*
Kawai et al., Chem. Pharm. Bull., vol. 44, No. 8, pp. 1425-1430 (1996).*
Emara et al., Analytica Chimica Acta, vol. 489, No. 1, pp. 115-123 (2003).*
Galvan-Tejada et al., Journal of Inorganic Biochemistry, vol. 91, pp. 339-348 (2002).*
Addison, C.C., et al.; *Ultraviolet Spectra of Anhydrous Metal Nitrates*; Journal of the Chemical Society (A); 1966, 1524-1528.
Afanas'ev, I.B., et al.;*Enhancement of Antioxidant and Anti-Inflammatory Activities of Bioflavanoid Rutin by Complexation with Transition Metals*; Biochemical Pharmacology; 61; 2001, 677-684.
Agatonovic-Kustrin, et al., *Spectrophotometric Determination of Furosemide and its Palladium (II) Complex*, Journal of Pharmaceutical & Biomedical Analysis, vol. 8, Nos. 8-12, 1990, pp. 983-986.
Akers, et al., *Alterations in Absorption of Dicumarol by Various Excipient Materials*, Journal of Pharmaceutical Sciences, vol. 62, No. 3, Mar. 1973, pp. 391-395.
Almöf, J., et al.; *An Investigation of Correlation Effects in Transition-Metal Sandwich Complexes. Hartree-Fock Studies on a Series of Metallocenes*; Chemical Physics Letters; 106 (4); 1984, 266-269.
Almof, J., et al.; *The Geometry and Bonding of Magnesocene an ab initio MO-LCAO Investigation*; Journal of Organometallic Chemistry; 249; 1983, 303-313.
Ambre, M.D., et al., *Effect of Coadministration of Aluminum and Magnesium Hydroxides on Absorption of Anticoagulants in Man*, Clinical Pharmacology and Therapeutics, vol. 14, No. 2, pp. 231-237, 1973.
Anderegg, G.; *Correlation Between Thermodynamic Functions of Metal Complex Formation and Basicities of the Iminodiacetate Derivatives*; 180; 1991, 69-72.

(Continued)

Primary Examiner — Porfirio Nazario Gonzalez
(74) Attorney, Agent, or Firm — Brinks Hofer Gilson & Lione; Ryan L. Marshall

(57) ABSTRACT

A metal coordination complex of a biologically active moiety and a metal is disclosed. The complex confers to the biologically active moiety an improved performance which can include potency, stability, absorbability, targeted delivery, and combinations thereof.

29 Claims, 20 Drawing Sheets

OTHER PUBLICATIONS

Baker, W.A., et al.; *Metal Binding in Tetracyclines. Cobalt (II) and Nickel (II) Complexes*;Journal of the American Chemical Society; 88(6); 1966, 1314-1317.

Barcelo-Oliver et al., Journal of Inorganic Biochemistry, 2004, vol. 98, p. 1703-1711.

Berezin, B.D.; *Coordination Compounds of Porphyrins and Phthalocyanines*; John Wiley & Sons, New York, NY, 1981; 13-15, 107-108.

Berge, S.M., et al., D.C.; *Review Article: Pharmaceutical Salts*; Journal of Pharmaceutical Sciences; 66 (1); 1977, 1-19.

Berners-Price, S.J., et al.; *Coordination Chemistry of Metallodrugs: Insights into Biological Speciation from NMR Spectroscopy*; Coordination Chemistry Reviews; 151; 1996, 1-40. (Abstract).

Bighley, et al., *Chelates of Dicumarol I: Preparation and Structure Identification of Magnesium Chelate*, Journal of Pharmaceutical Sciences, vol. 66, No. 8, Aug. 1977, pp. 1124-1127.

Binder et al., Gastroenterology, 1998, vol. 115, p. 1295-1301.

Bontchev, et al., *Copper(II) complexes of blood pressure active drugs*, Transition Metal Chemistry, vol. 27, 1-21, 2002.

Briganti, F., et al.; *Carbonic Anhydrase Inhibitors. Metal Complexes of 5-(2-Chlorophenyl)-1,3,4-thiadiazole-2-sulfonamide with Topical Intraocular Pressure Lowering Properties: The Influence of Metal Ions Upon the Pharmacological Activity*; Journal of Enzyme Inhibition; 15; 2000, 185-200.

Buschmann, H.J., et al.; *Complexation of Alkaline Earth (Group 2A) Cations by Noncyclic, Macrocyclic and Macrobicyclic Ligands in Propylene Carbonate Solutions*; Thermochimica Acta; 211; 1992, 13-20. (Abstract).

Chakrawarti, et al., *Study of Metal Complexes of Ampicillin*, Proceedings of the National Academy of Sciences, India vol. LXI, Section A, Part III, 277-284, 1991.

Chakrawarti, P.B., et al.; *Study of Metal Complexes of Ampicillin*; Proceedings of the National Academy of Sciences, India, Section A; Physical Sciences; 61(3); 1991, 277-284. (Abstract).

Chisholm, M.H., et al.; *Coordination Chemistry and Reactivity of Monomeric Alkoxides and Amides of Magnesium and Zinc Supported by the Diiminato Ligand CH(CMeNC$_6$H$_3$-2, 6-$^i$Pr$_2$)$_2$. A Comparative Study*; Inorganic Chemistry; 41; 2002, 2785-2794.

Chohan, et al., *Antibacterial and Antifugal Mono- and Di-substituted Symmetrical and Unsymmetrical Triazine-derived Schiff-bases and their Transition Metal Complexes*, Journal of Enzyme Inhibition and Medicinal Chemistry, vol. 19, No. 2, 161-168, 2004.

Chohan, et al., *Binding of Transition Metal Ions [Cobalt, Copper, Nickel and Zinc] withFuranyl-, Thiophenyl-, Pyrrolyl-, Salicylyl- and Pryidyl-Derived Cephalexins as Potent Antibacterial Agents*, Journal of Enzyme Inhibition and Medicinal Chemistry, vol. 19, No. 1, 51-56, 2004.

Chohan, et al., *Isatin-derived Antibacterial and Antifungal Compounds and their Transition Metal Complexes*, Journal of Enzyme Inhibition and Medicinal Chemistry, vol. 19, No. 5, 417-423, 2004.

Cook, D.H., et al.; *Seven-Coordination in Metal Complexes of Quinquedentate Macrocyclic Ligands. Part 6. Magnesium Complexes of Macrocyclic Ligands Containing Nitrogen and Oxygen Donor Atoms*; Journal of the Chemical Society, Dalton Transactions: Inorganic Chemistry; 5; 1977, 446-449. (Abstract).

Cotton, F.A. et al.;*Sulfoxides as Ligands. I. A Preliminary Survey of Methyl Sulfoxide Complexes*; Journal of the American Chemical Society; 82; 1960; 2986-2991.

Cowan, J.A. editor; *The Biological Chemistry of Magnesium*; VCH Publishers, Inc.; New York, NY; 1995; 1-21, 85-108 and 111-117.

Crowder et al., Biochemistry, 1996, vol. 35, p. 12126-12132.

Davis S., The Copper Complexes of amino acids, 1956, p. 759-766.

De Jong et al., JBC, 2003, vol. 278, No. 27, p. 24302-24307.

Evans, D.A. et al.; *Diastereoselective Magnesium Halide-Catalyzed anti-Aldol Reactions of Chiral N-Acyloxazolidinones*; J. Am. Chem. Soc.; 124 (3); 2002, 392-393.

Evans, I.P., et al.; *Dichlorotetrakis (dimethylsulphoxide) ruthenium(II) and its Use as a Source for Some New Ruthenium(II) Complexes*; Journal of the Chemical Society, Dalton Transactions; 1973, 204-209.

Faegri, K., et al.; *Molecular Structures of Alkaline-Earth-Metal Metallocenes: Electron Diffraction and ab Initio Investigations*; Organometallics; 9; 1990, 372-379.

Flammengo, R., et al., *Heme-Protein Active Site Models via Self-Assembly in Water*; Organic Letters, 5 (19); 2003, 3367-3370.

Fujii, T.; *Alkali-Metal Ion/Molecule Association Reactions and Their Applications to Mass Spectrometry*; Mass Spectrometry Reviews; 19; 2000, 111-138.

Futaki, S., et al.; *Arginine Carrier Peptide Bearing Ni(II) Chelator to Promote Cellular Uptake of Hisitidine-Tagged Proteins*; Bioconjugate Chemistry; 15; 2004, 475-481.

Gary A. Quamme, American Journal of Physiology, vol. 241, No. 4, pp. F340-F347 (1981).

Gerard, C., et al.; *Stability of Metal Complexes with Ligands of Biological Interest: Dopamine and Adrenaline*; Bulletin de la Societe Chimique de France; 134 (10-11); 1997, 1069-1074. (Asbstract).

Golcu, et al., *Synthesis and Characterization of Metal Complexes of Acebutolol, Atenolol, and Propanolol Antihypertension Drugs*, Synthesis and Reactivity in Inorganic and Metal-Organic Chemistry, vol. 34, No. 7, 1259-1275, 2004.

Golcu, et al., *Synthesis of Binuclear Copper (II) Complex of the Antihypertensive Drug Pindolol*, KSU Journal of Science and Engineering, vol. 8, No. 1, 4-9, 2005.

Grundy, J., et al.;*A New Class of Linked-bis (N,N'-dialkylamidinate) Ligand: Applications in the Synthesis of Bimetallic Aluminum Complexes*, Journal of Organometallic Chemistry; 662 (1-2); 2002, 178-187. (Abstract).

Hartmann et al., *Zinc Complexes of Sulfonamides*, Journal of Chemical Sciences, vol. 49, 1725-1730, 1994. (English Abstract).

Hartmann, et al., *Functional Zinc Complexes of Tris(midazolymethyl)amine Ligands*, Chem. Ber., vol. 127, 2123-2127, 1994. (English Abstract).

Herbst, W., et al., *Industrial Organic Pigments*; VCH Publishers, Inc., New York, NY; 1993; 21, 392.

Hondrellis et al., Monatshefte fur Chemie, 1988, vol. 119, p. 1091-1101.

Ichiyanagi, T., et al.; *Enantioselective Diels-Alder Reaction Using Chiral Mg Complexes Derived from Chiral 2-[2[Alkyl- or 2-[2-[(Arylsulfonyl)amino]phenyl]-4-phenyl-1,3-oxazoline*; Journal of Organic Chemistry; 62 (23); 1997, 7937-7941.

Ikeda et al., Japan Journal of Pharmacol., 1997, vol. 75, p. 165-169.

Jordan et al., Nature, 1999, vol. 399, p. 697-700.

Kiraly, R., et al.; *Metal Ion Binding to Daunorubicin and Quinizarin*; Inorganica Chimica Acta; 67; 1982, 13-18.

Kovala-Demertzi, D., et al.;*Metal Complexes of the Anti-Inflammatory Drug sodium [2-1(2, 6- Dichlorophenyl)amino[phenyl]acetate (Diclofenac sodium). Molecular and Crystal Structure of Cadmium Diclofenac*; Polyhedron; 12 (11); 1993, 1361-1370.

Lach, et al., *Diffuse Reflectance Studies of Solid-Solid Interactions*, Journal of Pharmaceutical Sciences, vol. 59, No. 9, Sep. 1970, pp. 1261-1264.

Lambs, L., et al.; *Metal Ion-Tetracycline Interactions in Biological Fluids. Part 7. Quantitative Investigation of Methacycline Complexes with Ca(II), Mg(II), Cu(II) and Zn(II) Ions and Assessment of their Biological Significance*; Inorganica Chimica Acta; 151; 1988, 33-43.

Lamer, J., et al. *Isolation, Structure, Synthesis, and Bioactivity of a Novel Putative Insulin Mediator. A Galactosamine chiro-Inositol Psuedo-Disaccharide Mn$^{2+}$ Chelate with Insulin-like Activity$^\#$*; J. Med. Chem.; 2003, 46, 3283-3291.

Lutz, M., et al.; *Authentication of Aminomethyl(hydrogen)phosphonate Coordination to a Main Group Metal: Synthesis and Crystal Structure of [Mg(O$_3$PCH$_2$NH$_3$)$_2$(H$_2$O)$_2$]2H$_2$O*; Inorganica Chimica Acta; 232; 1995, 189-193.

Martell, A.E., et al..; *Chemistry of the Metal Chelate Compounds*, Prentice-Hall, Inc. Englewood Cliffs, NJ; 1962;181-237.

McCallister, J.D.; et al., *Diffuse Reflectance Studies of Solid-Solid Interactions IV: Interaction of Bishydroxycoumarin, Furosemide, and Other Medicinal Agents with Various Adjuvants*, Journal of Pharmaceutical Sciences, 1970, 59, No. 9, 1286-1289.

Ming, L.-J.; *Structure and Function of "Metalloantibiotics"*; Medical Research Reviews; 23(6); 2003, 697-762.

Miyamoto et al., Molecular endocrinology, 1993, vol. 7, p. 224-231.

Mizuguchi, J., et al.; *Interpretation of the Near-Infrared Absorption of Magnesium Phthalocyanine Complexes in Terms of Exciton Coupling Effects*; J. Phys. Chem. A; 103 (41), 1999, 8193-8199.

Mizuguchi, J.; *Interactions of Magnesium Phthalocyanine as Evaluated by Energy Partition Analysis*; J. Phys. Chem. A; 105 (47), 2001, 10719-10722.

Mojumdar, S.C., et al.; *Thermal Decomposition and IR Spectra of Mg(II) Compounds with Caffeine*; Chemical Papers; 53(5); 1999, 309-314. (Abstract).

Muller, J.G., et al.; *Metallodrug Complexes that Mediate DNA and Lipid Damage via Sulfite Autoxidation: Copper (II) Famotidine and Iron (III) Bis(Salicylglycine)*; Inorganica Chimica Acta; 275-276; 1998, 314-319.

Murakami et al., Bulletin of the Chemical Society of Japan, 1964, vol. 37, No. 2, p. 268-272.

Nijenhuis et al., Kidney International, 2003, vol. 64, p. 555-564.

Nolan, K.B., et al.; *Synthesis and Characterization of Copper(II), Zinc(II) and Cobalt(II) Complexes of Salicylglycine, a Metabolite of Aspirin*; Inorganica Chimica Acta; 230; 1995, 209-210.

Ohyama, T, et al.; *Calorimetric Studies of Metal Binding to Tetracycline. Role of Solvent Structure in Defining the Selectivity of Metal Ion-Drug Interactions*; Inorganic Chemistry; 34; 1995, 3083-3086.

Orita et al., Arzneim.-Forsch. (Drug Res.), vol. 26, No. 1, pp. 11-13 (1976).

Paluchowska, B., et al.; *Direct and Outer-Sphere Coordination of the Magnesium Ions in the Crystal Structures of Complexes with 2-Furancarboxylic Acid (I) and 3-Furancarboxylic Acid (II)*; Journal of Chemical Crystallography; 27(3); 1997, 177-182. (Abstract).

Park, G., et al.; *Zinc and Copper Complexes of Prodigiosin: Implications for Copper Mediated Double-Strand DNA Cleavage*; Organic Letters, 5 (2); 2003, 113-116.

Parrill, A.L., et al..; *HIV Integrase Inhibitor Interactions with Active-Site Metal Ions: Fact or Fiction?*; in Computational Organometallic Chemistry; ed. Cundari, T.R.; Marcel Dekker, Inc., New York, NY; 2001; 189-196.

Pecoraro, V.L., et al.; *Stability Constants of $Mg^{2+}$ and $Cd^{2+}$ Complexes of Adenine Nucleotides and Thionucleotides and Rate Constants for Formation of Dissociation of Mg ATP and Mg ADP*; Biochemistry; 23(22); 1984, 5262-5271.

Pierloot; K.; *Nondynamic Correlation Effects in Transition Metal Coordination Compounds*; in Computational Organometallic Chemistry; ed. Cundari, T.R.; Marcel Dekker, Inc., New York, NY; 2001; 123-158.

Rajan, et al., *Metal Chelates of L-DOPA for Improved Replenishment of Dopaminergic Pools*, Brain Research, vol. 107, 1976, pp. 317-331.

Robinson, G.H., et al.; *Unusual Trimetallic Magnesium Cations and Adamantyl Anions of Aluminum and Gallium*, Journal of Organometallic Chemistry; 666; 2003, 7-13.

Schwendeman, S.P., et al.; *Comparison of the Effects of $Mg(OH)_2$ and Sucrose on the Stability of Bovine Serum Albumin Encapsulated in Injectable Poly(D,L-lactide-coglycolide) Implants*; Biomaterials; 23; 2002, 239-245.

Schwietert, C.W., et al.; *Coordination Compounds in Medicinal Chemistry*; Coordination Chemistry Reviews; 184(1); 1999, 67-89.

Sham, S., et al.; *Solid-State 25Mg Study of Inner-Sphere Mg2+ Binding Complexes*; Inorganic Chemistry; 39(1); 2000, 4-5. (Abstract).

Skorey, et al., JBC, 1997, vol. 272, No. 36, p. 22472-22480.

Supuran, C.T., et al.; *Carbonic Anhydrase Inhibitors. Inhibition of Isozymes I, II and IV with Heterocyclic Mercaptans, Sulfenamides, Sulfonamides and their Metal Complexes*; Journal of Enzyme Inhibition; 13; 1998, 177-194.

Supuran, C.T., et al.; *Carbonic Anhydrase Inhibitors. Part 60. The TopicalIntraocular Pressure-Lowering Properties of Metal Complexes of a Heterocyclic Sulfonamide: Influence of the Metal Ion Upon Biological Activity*; European Journal of Medicinal Chemistry; 34; 1999, 585-595.

Surks et al., JBC, 1989, vol. 264, No. 17, p. 9820-9826.

Sweeney et al., Biochemical Pharmacology, Aug. 2003, vol. 66, p. 663-677.

Turel, I., et al.; *Complex Formation Between Some Metals and a Quinolone Family Member (Ciprofloxacin)*; Polyhedron; 15(2); 1996, 269-275.

Valenti, et al., *The Effect of Saturation With Zn.sup.2+ and Other Metal Ions on the Antibacterial Activity of Ovotransferrin*, Medical Microbiology and Immunol, vol. 176, No. 3, 1987, pp. 123-130.

Vedejs, E., et al.; *Dual Activation in the Esterification of Hindered Alcohols with Anhydrides Using $MgBr_2$ and a Tertiary Amine*; Journal of Organic Chemistry; 61 (17); 1996, 5702-5703.

Wessels, J.M., et al.; *The Complexation of Tetracycline and Anhydrotetracycline with $Mg^{2+}$ and $Ca^{2+}$ : A Spectroscopic Study*; Journal of Physical Chemistry, B; 102; 1998, 9323-9331.

Wilkinson, R.; *Absorption of Calcium, Phosphorus and Magnesium, in Calcium, Phosphate and Magnesium Metabolism*; ed. Nordin, B.E.C.; Churchill Livingstone, Edinburgh; 1976; 106.

Williamson, D.E., et al.; *A Proton Nuclear Magnetic Resonance Study of the Site of Metal Binding in Tetracycline*; Journal of the American Chemical Society; 97(9); 1975, 2397-2405.

Winter, C.H., et al.; *Synthesis and Characterization of Cyclopentadienyl Thiolato Complexes of Magnesium*; Journal of Organometallic Chemistry; 669 ; 2003, 37-43.

Winter, C.H., et al.; *Synthesis, Structure and Properties of Magnesium Complexes Containing Cyclopentadienyl and Amidinate Ligand Sets*; Journal of Organometallic Chemistry; 682; 2003, 224-232.

\* cited by examiner

Outer sphere RNA:Magnesium Coordination Complex

R = Rest of RNA molecule
Base = Purine or pyrimidine

Inner sphere RNA:Magnesium Coordination Complex

RNA:Magnesium: Arginine Coordination Complex

Proton NMR of Bis(triiodothyroninato)-
bis(dimethylsulfoxide)magnesium

Proton NMR of Triiodothyronine (T3)

Proton NMR of Bis(triiodothyroninato)zinc

Proton NMR of Dimethylbiguanide:Zinc Complex

Proton NMR of Dimethylbiguanide

Proton NMR of Tetracycline

Proton NMR of Bis(tetracyclinato)magnesium

Proton NMR of Tetracycline-magnesium complex with 1N HCl added.

Proton NMR of Tetracyline with 1N HCl added.

Proton NMR of Hydrochlorothiazide

Proton NMR of Hydrochlorothiazide-Zinc Complex

Proton NMR of Hydrochlorothiazide-Zinc Complex with 1N HCl added

Proton NMR Bis(acycloguanosinato)magnesium

Bis(triiodothyroninato)-bis(dimethylsulfoxide)magnesium

Bis(triiodothyroninato)zinc

Bis(minocyclinato)magnesium

Bis(tetracyclinato)magnesium

Dimethylbiguanide-zinc complex

Bis(acycloguanosinato)magnesium

Pharmacokinetic Profile of T3, T3Mg, T3Zn in a Rat Animal Model

IEF evaluation of magnesium and zinc iRNA complexes.

METAL COORDINATED COMPOSITIONS

RELATED APPLICATIONS

This application is a continuation of prior application Ser. No. 12/317,931, filed Dec. 30, 2008 (U.S. Pat. No. 7,989,440), which in turn is a continuation of prior application Ser. No. 11/257,504, filed Oct. 24, 2005, now abandoned which in turn claims the benefit of U.S. Provisional Application No. 60/621,747, filed Oct. 25, 2004. The entire contents of all three of these documents are incorporated herein by reference, except that in the event of any inconsistent disclosure or definition from the present specification, the disclosure or definition herein shall be deemed to prevail.

FIELD OF THE INVENTION

This invention relates to novel metal coordinated complexes of biologically active molecules.

BACKGROUND OF THE INVENTION

It is desirable to improve the properties of known, biologically active molecules by modifying their structures. The goal of such modifications is a molecule that is improved in some way, such as potency, stability, reduced side effects, or targeted delivery. This improvement is achieved without sacrificing the molecule's desirable properties. While this goal is easily stated, it is difficult to achieve in actual practice, as the effects of any particular modification is often highly unpredictable.

SUMMARY OF THE INVENTION

According to the current invention, the structure of known biologically active molecules is modified to result in new molecules known as metal coordinated complexes. These new molecules have unexpectedly superior properties. The metal coordinated complexes of the current invention include complexes of thyronine, tetracycline antibiotics, oxycodone and hydrocodone, and complexes of their derivatives.

Chelation is a critical component in the stabilization of a metal coordinated complex. For the s-block metals, this is particularly true for calcium and magnesium. For example, it can be seen that the log $K_{eq}$ of the acetic acid-magnesium complex is 0.47. With the incorporation of a single amino group on the molecule (i.e., glycine) the log $K_{eq}$ increased to 1.34. Magnesium typically prefers chelation with oxygen over nitrogen and this effect can be seen by comparing the log $K_{eq}$ of adenine (log $K_{eq}$=2.08) with that of 6-hydroxypurine (log $K_{eq}$=6.65). Magnesium forms particularly strong bonds with oxidized phosphorus, such as phosphates, as is revealed by comparing the log $K_{eq}$ of adenosine (log $K_{eq}$=0.50) with that of adenosine-5'-monophosphoric acid (log $K_{eq}$=1.80).

In general, zinc complexes are more stable then the comparable magnesium complexes. This is particularly true if the ligand bears nitrogen or sulfur. (This may not be the case for ligands with oxygen only and even less so if the ligand is a phosphate.) Using the glycine example above, the log $K_{eq}$ for the glycine-zinc complex is 4.85. The strength of the zinc sulfur bond versus the oxygen bond is manifest in the relative log $K_{eq}$ values for the zinc complexes of hydroxypropanoic acid (log $K_{eq}$=0.86) and mercaptopropanoic acid (log $K_{eq}$=6.43). Comparisons of log $K_{eq}$ values with other metals and ligands reveal that this chelation stabilization prevails in metal coordination chemistry.

Whereas it may not be required that chelation occur to form a stable metal coordinated complex with inherent covalency, and this is particularly true with the transition metals combined with nitrogenous ligands, in most cases it is a preferred embodiment of this invention that the active agent chelate with the metal, particularly if the metal is magnesium.

It is an embodiment of this invention that the active agents that make the best candidates for complexing with magnesium and calcium are those that have a proton on a heteroatom (i.e., oxygen, nitrogen or sulfur) with a $pK_a$ slightly greater than water or lower than water and have an additional heteroatom in close proximity to the first protonated heteroatom such that it can participate in the bonding, or otherwise chelate, with the metal. Drugs that have this arrangement of functional groups are most likely going to bond with a metal, where the resultant metal coordinated active agent will be stable enough in a biological system and survive hydrolysis therein, such that the performance of the active agent will be sufficiently modulated. This hydrolytic stability imparted by multidentate ligands is supported by the fact that they can lower the $pK_a$'s of the ligand such that even amides can be deprotonated with weak bases, such as triethylamine, in the presence of coordinating metals. Therefore, active agents with protons on heteroatoms, which normally would not be ionized in typical biological pH, can have the proton replaced with a covalently coordinated metal, where covalency is enhanced by the additional chelation from participating heteroatoms. It is a preferred embodiment of this invention that at least one of the heteroatoms on the active agent that will bind to magnesium or calcium be oxygen or sulfur. Magnesium forms unusually strong bonds with phosphates and phosphonates and, therefore, it is an additional embodiment of this invention that the active agent coordinated with magnesium is an organophosphate or organophosphonate compound.

It is an embodiment of this invention that the active agents that make the best candidates for complexing with zinc and the p-block metals are the same as those with the s-block metals with the additional flexibility that if the active agent has two nitrogens, a nitrogen and a mercaptan or two mercaptans in a proper chelation arrangement, then the presence of a proton on a heteroatom is not necessary to form a stable metal coordinated complex. It is a further embodiment of this invention that transition metals have further ligation flexibility in that chelation is even less required for their covalent coordination complexes if the ligands have at least one nitrogen or mercapto group.

The active agents which are embodied in this invention can be divided into chemical classes as shown in Table 1 (actually they may be divided into combinations of chemical classes to reflect the heterogenous chelation potential). The drugs listed in Table 1 are not intended to be an exhaustive list of all drugs that satisfy the embodiment of this invention but a representation of the chemical classes that exist in pharmaceuticals and that other pharmaceuticals that are of the same class listed in Table 1 or have arrangements of atoms that is satisfied by the embodiments of this invention are also claimed by this invention.

TABLE 1

Biologically active molecules that form coordination complexes in accordance with the Invention.

| Chemical Class or Functional Group Combination | Therapeutic Classes | Drug Examples |
| --- | --- | --- |
| Guanide or diamine | Antidiabetic, AntiGERD, Antineoplastic, Antiviral, Antihypertensive | Metformin, Famotidine, Mitoxantrone, Adefovir, Hydralazine, Zanamivir |
| Amine or amide with sulfonamide | GERD, Diuretic, Antimigraine, Antidiabetic | Famotidine, Hydrochlorothiazide, Sumatriptan, Glipizde, Glyburide, Torsemide |
| Amine or amide with azole | GERD, Antiviral, antimigraine, Antiurolithic, Antihypertensive, Analgesic, Anitemetic | Lansoprazole, Zolmitriptan, Rabeprazole, Omeprazole, Esomeprazole, Ribavarin, Allopurinol, Clonidine, Granisetron |
| Amine or amide with alcohol | Antineoplastic, Antiviral, Bone resorption inhibitor, Antibiotic, Bronchodilator, Antithrombotic, Analgesic, Antihypertensive, Anxiolytic, Anticonvulsant | Mitoxantrone, Saquinavir, Alendronate, Albuterol, Ephedrine, Epinephrine, Dipyramidole, Oxycodone, Oxymorphone, Tetracycline, Minocycline, Doxycycline, Labetalol, Lorazepam, Oxazepam |
| β-diketone, α-diketone, ketophenol, α-ketoalcohol β-ketoalcohol | Antibiotic, Antineoplastic, Antiinflammatory, Multiple sclerosis treatment | Tetracycline, Minocycline, Doxycycline, Mitoxantrone, Atovaquone, Betamethasone, Paclitaxel, Docetaxel, Methylprednisolone, Prednisone, Idarubicin |
| β-ketoacid | Antibiotic | Levofloxacin, Ofloxacin, Norfloxacin |
| Ureide | Antiviral, Antiparkinsonian, Bronchodilator | Tenofovir, Acyclovir, Cabergoline, Theophylline, Valgancyclovir |
| Amine or amide with acid | Antihypertensive, Hormone replacement, Antiparkinsonian, Diuretic, Antipsoriatic, Antineoplastic, Antirheumatic, Antibiotic, Antiepileptic, Antidepressant, Analgesic | Quinapril, Ramipril, Trandolopril, Enalipril Lisinopril, Thyroxine, Liothyronine, DOPA, Furosemide, Methotrexate, Penicillin, Amoxicillin, Cefotetan, Captopril, Gabapentin, Ketorolac |
| Alcohol with azole | Angiotensin II receptor antagonist, | Losartan, |
| Phosphonate or phosphate | Bone resorption inhibitor, Antiviral | Alendronate, Etidronate, Fosamprenavir |
| Phosphonateor phosphate with amide | Antiepileptic | Fosphenytoin |
| Diol or polyol | Bronchodilator, Nutritional supplements, Contrast imager | Albuterol, Epinephrine, Myoinositol, Chiroinositol, Iodixanol |
| Mercaptan with acid | Antiasthmatic, Antibiotic | Montelukast, Cefazolin, Cefotetan |
| Mercaptan with amine or amide | Antipsychotic, Antihypertensive | Olanzapine, Captopril |
| Amine with amide | Hormone deficiency, Antibiotic | Tabimorelin, Amoxicillin, Loracarbef, Iodochlorohydroxyquin |
| Alcohol with acid | Analgesia, Cholesterol lowering, Antihypertensive Antiinflammatory | Salicylic acid, Atorvastatin, Mesalamine, Pravastatin, Sitofloxacin, Trovafloxacin |
| Dicarboxylic acid | Antineoplastic | Pemetrexed |
| Amine with N-oxide | Antialopecia agent | Minoxidil |
| Alcohol with Nitrites | Antibiotic | Metronidazole |
| Diene with alcohol, amine, amide or acid | Antiacne, Antineoplastic | Retinoic acid, Fenretinde |
| Oligonucleotide (polyureide or polyphosphate) | Gene therapy, Anti-AMD | iRNA, Pegaptanib |
| Oligopeptide (polyamide) | Immunosuppressant, Antianemic, Antiviral, Antineoplastic, Diuretic | Cyclosporin, Epoetin, Inteferon, Atrial Natriuretic Peptide, Abarelix |

TABLE 1-continued

Biologically active molecules that form coordination complexs in accordance with the Invention.

| Chemical Class or Functional Group Combination | Therapeutic Classes | Drug Examples |
|---|---|---|
| Oligosaccharide (polyol) | Anticoagulant, Antidiabetic, Antibiotic | Heparin, Acarbose, Gentamycin, Tobramycin |

GERD = Gastroesophageal Reflux Disease
AMD = Age-related Macular Degeneration

BRIEF DESCRIPTION OF THE DRAWINGS

For the present invention to be clearly understood and readily practiced, the present invention will be described in conjunction with the following figures, wherein.

DETAILED DESCRIPTION OF THE INVENTION

Figure 1:
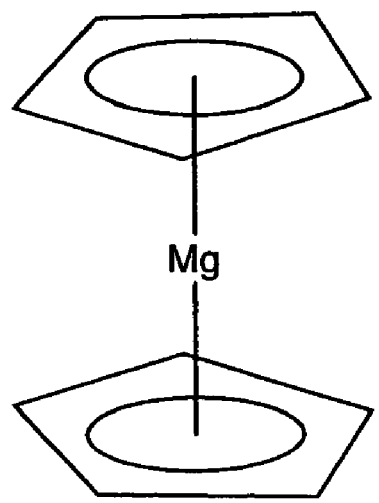
FIG. 1 illustrates the structure of Magnesocene in accordance with the prior art.

Chemical bonds exist in three basic forms: ionic, covalent and coordination or the so-called Werner complexes, which are typically larger than inorganic metal salts. (It should be pointed out that Werner complexes are considered to have neutral ligands.) The differences between the three bond types can be attributed, in part, to the thermodynamic stability of the bond, particularly in solution. Conversely, the stability of a compound can be expressed as the propensity for the atoms of the molecule to separate or dissociate in solution.

The thermodynamic stability of a compound is expressed in terms of it free energy of formation according to equation 1:

$$\Delta G = -RT \ln K \qquad \text{Equation 1}$$

Where ΔG is the Gibbs free energy and indicates the thermodynamic stability of the compound. The more negative ΔG is the more stable the compound. R is the gas constant, T is the absolute temperature and K is the equilibrium constant. The equilibrium constant is expressed as a ratio of products over reactants. In the case of coordination compounds for the reaction:

$$M + xL \longleftrightarrow ML_x$$

K is expressed in equation 2:

$$K = [ML_x]/[M][L]^x \qquad \text{Equation 2}$$

Thus the increasing thermodynamic stability of a compound is directly related to the increasing value of the equilibrium constant.

In certain cases it is advantageous to express the equilibrium constant in terms the dissociation potential of a metal-ligand bond. The reaction is thus:

$$ML_x \leftrightarrow M + xL$$

The dissociation constant, $K_{diss}$ is shown in equation 3:

$$K_{diss} = [M][L]^x/[ML_x] \qquad \text{Equation 3}$$

Whereas it is commonly accepted that ionic bonds nearly completely dissociate in solution, most covalent bonds, do not dissociate at all. Thus, determining bond strength in solution, through measurement of the dissociation constant or the more commonly expressed parameter the equilibrium constant, is a method of discerning the bond type. For coordination compounds, which involve bonding between metals and ligands from Groups 15-17, the thermodynamic stabilities have not been firmly established.

Examination of the literature reveals that covalency of organometallic bonds can be determined from spectroscopic data (i.e. NMR and MS), ab initio molecular mechanics calculations or a combination of the two. In general, covalency is most likely to occur with transition metals, with nitrogen and sulfur ligand atoms (in preference to oxygen) and with increasing bond order or haptivity (designated "η") from the ligand. Organometallic compounds with ligands that having multiple haptivities are described as chelates. Amongst the metals in groups 1 and 2, the so called s-block main group elements, only beryllium and magnesium are considered to be important chelate forming elements.

Recent research, using ab initio theoretical calculations, has further qualified the nature of the coordination bond in terms of the ionic vs. covalent nature of the ligand-metal bond. Pierloot applied the CASSCF (complete active-space self-consistent field) model to a series of Werner complexes to measure the degree of covalency of these organometallic complexes. Her general conclusions were that a trend exists wherein the static correlation energy, obtained from the CASSCF calculations, correlates well with covalency of the metal-ligand bond. She further concluded, that for the same metal, the metal-ligand covalency and related correlation effects increase in the following order of ligands:

$$F^- < OH_2 < NH_3 < Cl^- < Br^- < I^-.$$

This was in agreement with the nephelauxetic effect described by Jørgensen. The magnitude of this effect was directly correlated to the reduction of the interelectronic repulsion of a transition metal upon coordination in a ligand field. This reduction depended on the ligands and was expressed as the ratio of the Racah parameter, B, in the complex and in the free metal ion ($\beta = B_{complex}/B_{ion}$). The reduction in B resulted from a decrease in electron-electron repulsion of the free metal ion after ligands were added to form the metal complex; a large reduction in B indicates a strong nephelauxetic effect. Thus ionic ligands, such as F⁻, give a small reduction in B and have larger β values. Based on spectroscopic measurements, ligands were ordered according to decreasing β values generating the nephelauxetic series:

$$F^- > OH_2 > (NH_2)_2CO > NH_3 > H_2NCH_2CH_2$$
$$NH_2 \approx (COO)_2{}^{2-} \approx (CO_3)^{2-} > NCS^- > Cl^- > CN^- >$$
$$Br^- > N_3{}^- > I^- > S^{2-} \approx (C_2H_2O)PS_2{}^{2-} > \text{diarsine}$$

The correlation of the two series is supported by the similarities between the effects that both techniques described. In the former case, the CASSCF calculation gauges the contribution of the metal d-orbital to the metal-ligand bond. Racah parameter reduction by complex formation ($B_{complex}$) is caused by delocalization of the transition metal d-orbital electron cloud on the ligands, which is indicative of covalent bond formation.

Bonding between Li⁺ and Be²⁺ with Cp ligands is mostly ionic due to the low energy state of the contributing metal bond relative to the Cp bond. In addition, the ionic radius of these elements is too small to allow more than one Cp ligand to bond.

Theoretical calculations of magnesocene (FIG. 1), $Cp_2Mg$, reveal that the structure of the compound resembles that of $Cp_2Ca$, $Cp_2Sr$ and $Cp_2Ba$ but the d-orbital populations of Mg were found to be negligible in $Cp_2Mg$. However, the Mulliken charge for Mg in $Cp_2Mg$ using the density functional theory (DFT) model predicted 0.66; a value close to 2 is expected for a compound with a large dissociation constant such as $MgCl_2$. This is in agreement with a paper by Faegri, Almlöf and Lüthi, who, according to ab initio MO-LCAO calculations conclude that the charge separation of magnesocene is only slightly higher than that of ferrocene ($Cp_2Fe$), a known covalent coordination compound. These data would suggest that the Mg-Cp bond is somewhat covalent. The Cp moiety contributes its covalent bonding partly from its negative charge and partly from Π-bonding from the double bonds. This combination of anionic and Π-bonding with metals would also occur in retinoic acid and its analogs. Thus forming metal coordinated compounds of retinoic acid is an embodiment of this invention.

Figure 2:
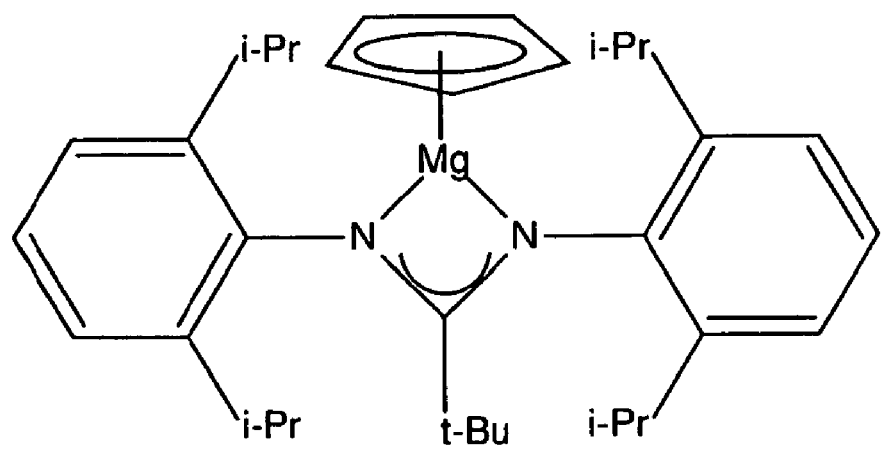
FIG. 2 illustrates the structure of (Cyclopentadienyl)-$^t$butylmethylbis(N,N'-[2,6-diisopropylphenyl]amidinate)magnesium in accordance with the prior art.

The reactivity of $Cp_2Mg$ and related Mg-Cp compounds was studied by Winter, et. al., and they found that magnesium forms stable bonds with amidinate ligands. Perhaps most telling was the stability of [CpMg(η²-ᵗBuC(N(2,6-ⁱPr₂C₆H₃))₂)], which was sublimed unchanged with 80% recovery at 180° C./0.05 torr (FIG. 2). Thus an example of a stable magnesium-amidinate compound has been reported, which provides further support to the covalency of such compounds. This is important for compounds that contain amidinate functionalities such as the purine and arginine containing compounds.

Whereas it is commonly accepted that transition metallocenes have strong covalent character, a legitimate argument that main group metallocenes have significant covalent bond elements has been made as well. The lack of d-orbital participation in the metal-ligand bonding may reduce the stability of the compound but does not preclude the notion that main group metals, particularly magnesium, can form bonds with ligands that are more covalent than ionic. It is generally known that the formation of 6-coordinate magnesium complexes upon their crystallization is due to $sp^3d^2$ hybridization. So it is conceivable that in certain situations even the d-orbitals of magnesium can participate in bonding of the coordination complex.

Figure 3:
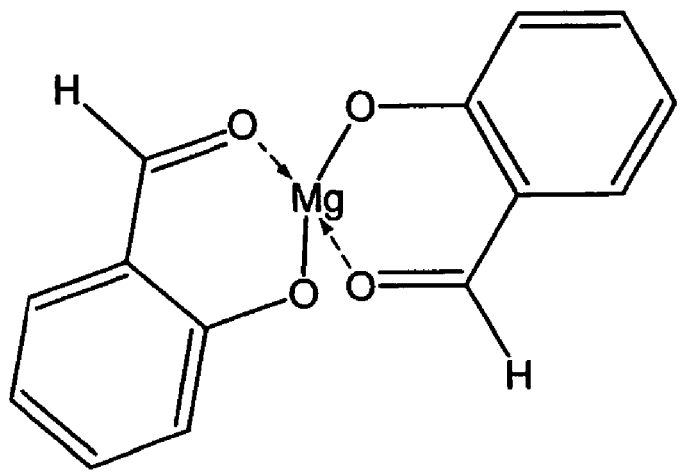
FIG. 3 illustrates the structure of magnesium:salicylaldehyde complex in accordance with the prior art.

One can see a large difference in stability when comparing the equilibrium constants of a Werner complex with a metal halide. For example, log $K_{Mg-pyridine}$=2.08 and log $K_{MgCl2}$≈−1.0. Keeping in mind that pyridine is a neutral ligand; this difference in log K can only be due to the covalency of the magnesium-pyridine bond vis-à-vis the ionic nature of the magnesium-chloride bond. Another example of a stable magnesium complex is seen with magnesium-salicylaldehyde (SA) complex, with a log $K_{Mg-SA2}$=6.80 (FIG. 3). The stability of this bond is remarkable in that the ligand bonding atom is oxygen, which typically tend to form ionic bonds with metals. However, the existence of chelating oxygen stabilized the complex beyond what a pure ionic bond would do. Although nitrogen will form stronger bonds to magnesium than calcium, typically oxygen is a stronger chelator of magnesium than nitrogen.

The equilibrium constants of chelates are typically very large (e.g., log $K_{eq}$ for magnesium ethylenediamine-N,N'-disuccinate complex is 6.09) and may not reveal the extent of covalency between the neutral part of the ligand and the metal. However, it is the equilibrium constant that dictates the stability of any coordination compound and that is an important criterion for determining the nature of the chemical entity and how it will perform in particular applications. The existence of a covalent bond within the complex and its contribution to the stability of chelates can explain their very large log $K_{eq}$ and may also contribute to the rigidity of the molecular structure. It should be pointed out that, in many cases, covalency is the most important contributor to the stability of a coordination complex.

Figure 4:
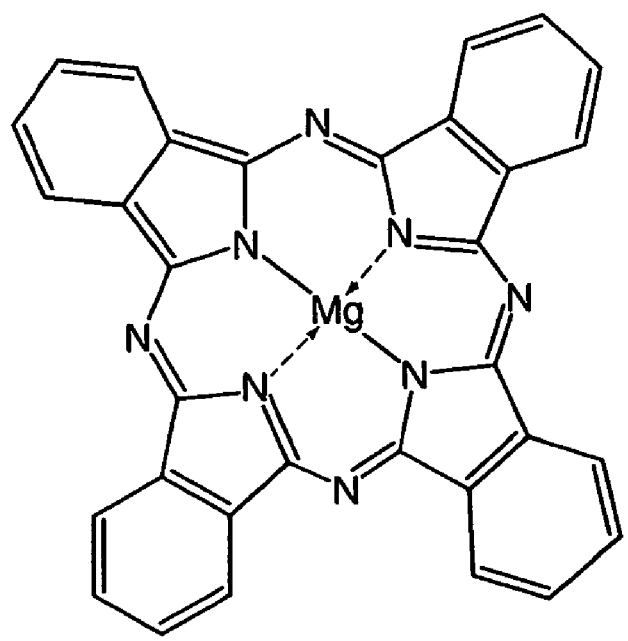
FIG. 4 illustrates the structure of Magnesium phthalocyanine in accordance with the prior art.

The magnesium porphyrin complexes or chelates are likely the most well known organomagnesium compounds; chlorophyll is a magnesium porphine. Phthalocyanine is a porphyrin representing the basic elements of that class of compound and is used extensively as a model system to study metal-porphyrin bonds. It has been determined that transition metals form complexes with phthalocyanine (FIG. 4) very easily but because alkali and alkali earth salts dissociate so completely in water and other protic solvents, no solvent has been found, so far, which is suitable for direct introduction of $Li^+$, $Na^+$, $K^+$, $Sr^{2+}$ and $Ba^{2+}$ from solutions of their salts. As predicted from the ease of complexation of $Mg^{2+}$ and $Be^{2+}$, only these two s-block elements along with $Ca^{2+}$, can be directly introduced into phthalocyanine, which is typically done from their iodide or perchlorate salts in pyridine.

The synthesis, structure, stability and physical properties of metal-porphyrin complexes have been well studied. The structure and the physical properties of magnesium phthalocyanine have been further elucidated using a variety of techniques, most recently, near-IR absorption and X-ray crystallography. The recurring conclusion is that the magnesium-porphyrin chelate represents an extremely stable example of a metal coordinated compound.

Certain magnesium-ligand complexes are indeed covalent in nature and not ionic and thus are new compositions of matter and not merely new salt forms. Metal-organic ligand compounds, covalency in the nature of their bonds.

It is an embodiment of this invention that the formation of a coordination complex is favored when the ligand has direct bonding opportunity to the inner sphere of the metal, preferably magnesium. This is accomplished by using anhydrous magnesium and non-protic solvents (or if the solvent is protic it should be bulky). This concept is supported by the fact that the catalytic reactivity of a metal ion is reduced in its hydrated form. Complex formation in aqueous systems is a delicate balance between hydrogen bonds between ligand and water and the competition for binding sites on the metal by hydration and complexation capability of the ligand. It follows that complexation of a ligand with the inner sphere of metal is also reduced in aqueous systems. It further follows that the converse is true—that is, the rate of chelation or complexation of metals with ligands in non-aqueous systems is accelerated vis-à-vis aqueous systems.

A composition comprising an organic active agent bound to a metal as a stable metal-ligand coordination compound with inherent covalency is as a new molecular entity. In another preferred embodiment of the invention, the metal is selected from the main group elements. In yet a further embodiment of the invention, the metal is selected from the s-block elements. In a preferred embodiment of the invention, the metal is magnesium.

Furthermore, it is an embodiment of this invention that virtually any drug-magnesium complex with a $K_{eq} > 1.0$ has enough inherent stability to modulate the pharmacokinetics of dissolution, absorption, distribution, metabolism and excretion. Given that the dissociation constant of $Mg(OH)_2$ is $-11.5$, it is not surprising to discover that most magnesium complexes are much more stable in alkaline conditions than in acid. Thus the stability of the drug-magnesium complex in the small intestines is likely to modulate the pharmacokinetics of drug absorption. For those metal-drug complexes that are acid labile, it is an embodiment of this invention that protection of the complex from the acidic milieu of the stomach be accomplished by a coating or encapsulation material that releases the complex upon entry into the small intestines. It is a further embodiment of the invention that the encapsulation agent is a ligand or group of ligands forming an outer coordination sphere.

Another important concept of this invention is that simple combinations of metal with ligands in solution do not always produce the same product. It is recognized that several, if not many, patents claim various salts as dependent claims without any support in the subject matter. This is accepted because the salt of an organic acid is easily prepared by treating it with a base and a metal salt where the expected product is the metal salt of the organic acid; a method known by anyone skilled in the art. However, when coordination chemistry contributes to the bonding between the organic acid and the metal, a variety of conditions, such as solvent, temperature and, perhaps most importantly, ligands attached to the metal, impact the structure and the stability of the coordination complex.

Additional ligands, other than the drug, can stabilize the metal-drug complex. For example the $K_{eq}$ of the glycine (G) magnesium bond is 1.34. If, however, salicylaldehyde is added to the complex, the equilibrium for the reaction

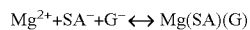

$$Mg^{2+} + SA^- + G^- \longleftrightarrow Mg(SA)(G)$$

is 4.77. Clearly salicylaldehyde adds a stabilizing effect to magnesium glycine bond. It is an embodiment of this invention, that adjuvants, like salicylaldehyde are incorporated into the drug:metal complexes to impart beneficial physicochemical properties. It is a further embodiment of this invention that the benefit of adjuvants is to stabilize the drug:metal complex in certain environments, such as in aqueous solutions.

There are very few examples of coordination complexes with transition metals found in the Physician's Desk Reference ("PDR") and include 1) insulin modified by zinc; 2) carboplatin contains platinum; 3) niferex is a polysaccharide-iron complex; 4) pyrithione zinc, used as the active ingredient in anti-dandruff shampoo. In addition, some nutritional supplements are described as complexes. Chromium picolinate is one example, where three picolinic acid groups are bound to a single $Cr^{+3}$ in an octahedron (the nitrogens provide the three other binding sites). Whereas it is an embodiment of this invention that the metal is selected from the group representing transition metals in a more preferred embodiment of the invention the metal is selected from the s-block main group elements, groups 1 and 2. In a most preferred embodiment of the invention the metal is magnesium.

The patent literature cites some examples of novel magnesium coordinated drugs, which include: 1) Trilisate® a stable, solid choline magnesium salicylate composition mentioned above for treating arthritic pain; 2) magnesium salts of 2-des-carboxy-2-(tetrazol-5-yl)-11-desoxy-15-substituted-omega-pentanorprostaglandins imparting greater tissue specificity and ease of purification and compounding into medicaments; 3) magnesium vanadate with insulinomimetic properties with utility in treating insulin resistance syndromes; 4) a crystalline magnesium-taurine compound for treatment of thrombotic or embolic stroke and prophylactic treatment of preeclampsia/eclampsia and acute cardiac conditions; 5) the magnesium omeprazole "salt" derivatives mentioned above to treat GERD.

The science of pharmaceuticals salts is a well studied area and selection of the salt form can impact a given pharmaceutical's performance. Examples of effects that the salt form can have on a drug include dissolution rate, solubility, organoleptic properties, stability, formulation effects, absorption modulation and pharmacokinetics. The periodical, Drug Delivery, published an article in October, 2003, citing three excipient applications using metals, presumably forming salts, to stabilize pharmaceutical agents. Human Growth Hormone is complexed with zinc to reduce its hydrophilicity and thereby slow the drug release; stabilization of proteins against the acidic environment produced by degradation of encapsulating polymers was accomplished by adding magnesium hydroxide to the formulation; zinc carbonate was used to stabilize vinca alkaloids from acid hydrolysis. Whereas these products clearly use metals to stabilize the pharmaceutically active agent, the latter two do not claim to have modified the structure of the active agent.

Further it is well established that by simply changing salt forms, the pharmacokinetics of absorption in the small intestines is significantly modulated. For example, the chemical structures of both the phosphate salt of tetracycline and tetracycline hydrochloride differ in that portion of the salt form which is not the pharmacophore and one would expect that the relative physical properties of each would not have a great influence on their relative bioavailabilities. But in fact, the phosphate salt is absorbed twice as much as the hydrochloride salt. Conversely, the bioavailability of the free acid of warfarin is nearly equivalent to its sodium salt, which is unexpected because the dissolution rate of the warfarin sodium tablet is 350 times faster than the tablet containing the free acid. If different salt forms can confer such changes in the kinetics of absorption, than a complex with an S-block main group element may have even a more pronounced effect on absorption.

It is known that the bioavailability of tetracycline antibiotics is mainly influenced by the physicochemical properties of their metal complexes that will most likely form in the GI tract. This is clearly an indication of drug:metal bond formation in vivo. The formation of a covalent bond between a drug and a metal in vivo is even a more reasonable expectation when the drug contains nitrogen and the metal is in Groups 10-12 (e.g., nickel, copper, zinc). It is an embodiment of this invention that modulation of a drug's performance is imparted by a formulation of the drug and the metal, which will facilitate formation of a stable complex between the drug and the metal.

It is an embodiment of this invention that the following benefits can be conferred upon a drug when complexed or coordinated with a metal:
1. Improved water solubility, which can equate to better bioavailability (see discussion below);
2. Enhanced lipophilicity for improved absorption through the cell membrane;
3. Locking the pharmacophore into a conformation for improved receptor binding;
4. Ameliorating formulation problems due to polymorphism (see discussion below);
5. Acid absorption properties for protection from degradation in acidic environments, such as the stomach;
6. The stability of the coordination complex may infer a delay in absorption of the active pharmacophore. This is important for drugs like liothyronine, where rapid absorption of the drug increases toxicity potential.
7. Bioadhesion properties for sustained absorption of the active pharmacophore;
8. Prevent abuse of narcotic analgesics by binding the pharmacophore through an organometallic complex to render the narcotic inert unless ingested.

Nature provides many examples of how transition metals are transported, stored and utilized. Perhaps the most well known example is hemoglobin, which is iron porphyrin. As stated earlier chlorophyll is a porphine structure surrounding magnesium. Some enzymes require metals in order for them to be active. That is the reason why trace metals, such as copper, zinc, chromium, etc. are important for proper nutrition. Even some antibodies have transition metals associated with them. The metal is required for enzyme activity due to the metal locking the peptide structure of the enzyme in a conformation through the formation of a coordination complex.

The concept of incorporating computer aided design of drugs has gained popularity in recent years. This technique, which has been referred to as in silico, has developed to the point that through the understanding of allosteric, coulombic and non-covalent interactions between the substrate and the receptor, lead drug candidates have been identified by computer modeling, before any material has been produced. It is an embodiment of this invention that by including metal coordination in the computer simulated molecule, new and improved lead compounds can be identified. It is a further embodiment of this invention that in silico derived lead compounds will have altered docking thermodynamics when the incorporation of a metal as a complex of the lead compound is included in the calculations. It is a yet further embodiment of this invention that compounds previously removed from consideration based on unsatisfactory in silico analyses will become important lead compounds when reanalyzed with the incorporation of a metal complex into the calculations. It is a preferred embodiment of this invention that the metal used for the revised in silico calculations as described above are selected from the main group elements. In a more preferred embodiment of this invention the metal is selected from the s-block main group elements. It is a preferred embodiment of this invention that the metal is magnesium.

In terms of direct application of the complex to a biological system, it is an embodiment of this invention that active agents that require ligand-receptor binding are imparted enhanced biological activity by virtue of the active agent's conformational structure being locked in place through complexation with a metal. The receptor can be membrane-associated, within the cytoplasm or circulating in the body. It is an embodiment of this invention that metals be incorporated into injectable drugs to lock the drug into a conformation that provides optimum interaction with its target receptor. It is a preferred embodiment of this invention that the metal be considered safe for injection. It is yet an even further embodiment of this invention that the metal be selected from the list of aluminum, bismuth, magnesium, calcium, iron or zinc. It is yet a further preferred embodiment of this invention that the active agent is selected from the list of injectable drugs, including, but not limited to, vaccines, antineoplastics, antidiabetic drugs, and antisense RNA or other metabolic modulators.

The metal coordination technology of this invention could also advance current research in vaccine design. For example, a new cancer vaccine being developed combines a lipoprotein adjuvant, a peptide antigen with a carbohydrate antigen specific for cancer cells. The three components of the vaccine construct are joined together covalently via linkers. This method of constructing the vaccine is common in bioconjugate chemistry. Metal coordination can be used as a scaffold to bind the different components of a bioconjugate such as Pegaptanib, whose combined components are an aptamer, polyethylene glycol and a lipid. It is an embodiment of this invention that the components of a bioconjugate can be combined in a single molecular entity by complexing each component to a central metal. It is a further embodiment of this invention that metal coordination serves as a general technique in bioconjugate chemistry.

Of particular note is the remarkable affinity that magnesium has for nucleic acids. With the advent of antisense RNA, interference RNA and aptamers as therapeutic agents it will be increasingly important to incorporate delivery technologies for these nucleic acid drugs. Some of the drug delivery techniques that are currently being investigated include pegylation, liposomes or anionic clays. Interestingly, a recent study released by Howard Hughes Medical Research Lab indicated that montmorillonite clay facilitated entry of RNA into lipid vesicles. There are a variety of clays that vary in the amount of alumina, silica, magnesia, iron and potassium. Thus, forming a magnesium complex of RNA may facilitate RNA's entry into vesicles, which are considered to be a laboratory model of cellular membranes.

Figure 5:
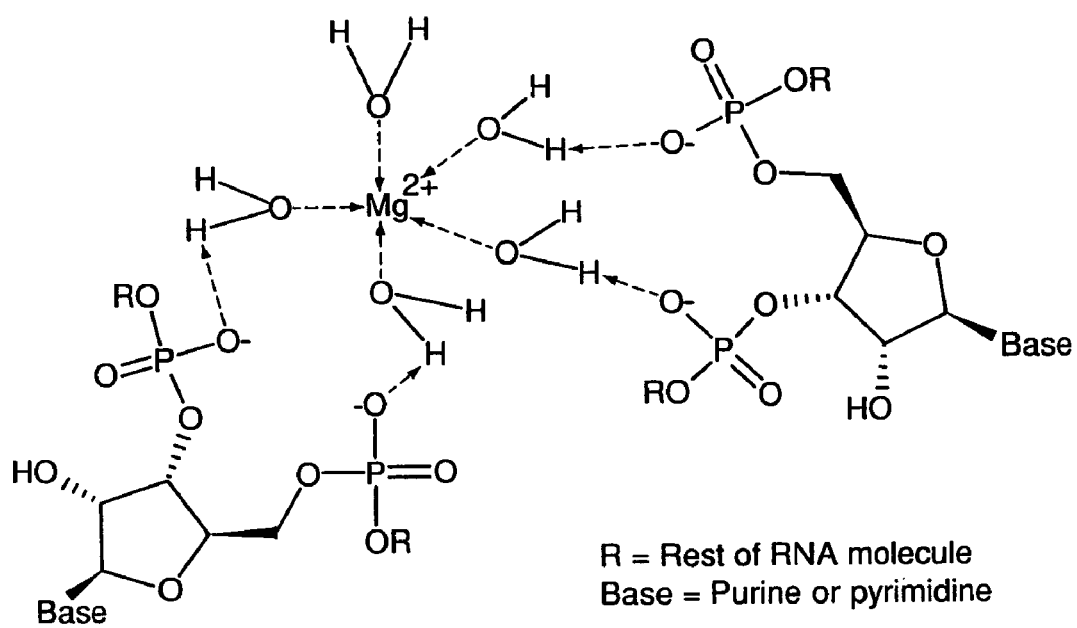
FIG. 5 illustrates an outer sphere RNA:magnesium coordination complex in accordance with the prior art.
Figure 6:
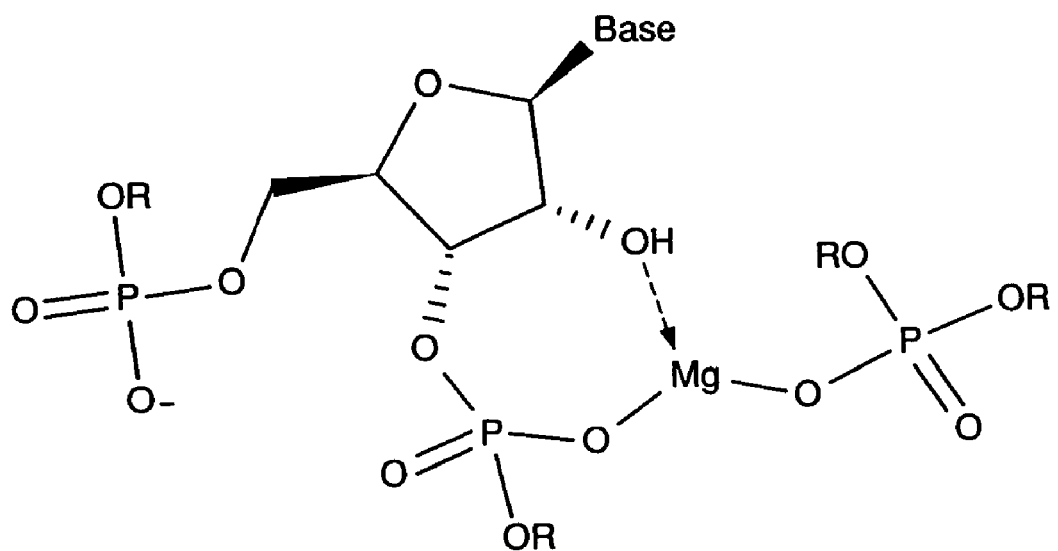
FIG. 6 illustrates an inner sphere RNA:magnesium coordination complex in accordance with the present invention.

The efficacy of the magnesium-nucleic acid complex can be evaluated vis-à-vis the nucleic acid alone using in silico techniques described above. Thus it becomes an important embodiment of this invention that nucleic acid drugs' efficacy is enhanced by their coordination with metals. It is a further embodiment of this invention that the nucleic acid be combined with a metal to form a coordination complex prior to administration. A significant portion of the complexes in simple combination of a metal salt with a nucleic acid in aqueous systems will be outer sphere coordinated ligands (FIG. 5) and may not provide the optimum conformation for receptor binding, particularly for membrane transport applications. A major premise of this invention is that metal-ligand complex structure is impacted significantly if the ligand has the opportunity to be an inner sphere ligand (FIG. 6) in preference to being an outer sphere ligand.

Figure 7:
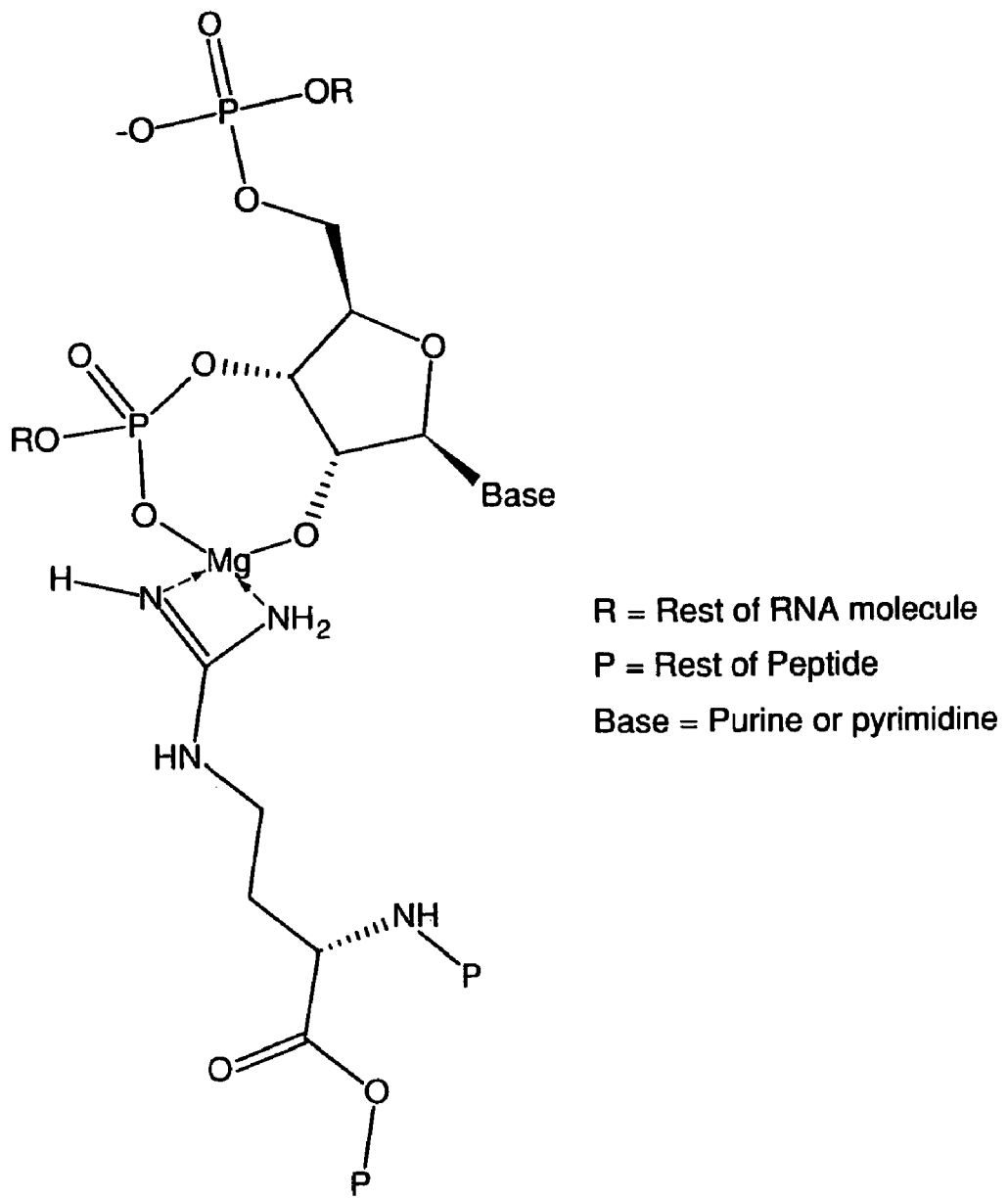
FIG. 7 illustrates an RNA:magnesium:arginine coordination complex in accordance with the present invention.

It is a further premise of this invention that inner sphere ligand formation is promoted by using anhydrous conditions to prepare the metal-ligand complex. It is an embodiment of this invention; therefore, that the metal ligand complex is prepared under anhydrous conditions and that reconstituting the complex in water will produce a coordination complex with greater covalency, greater stability, greater cell permeability and modulated biological performance relative to the complex prepared in water. This system is very amenable to incorporating adjuvants, such as polyarginine to enhance transfection efficiency, within the inner coordination sphere (FIG. 7).

Perhaps the most important development in recent times in gene therapy was the discovery and advanced research on interference RNA ("iRNA"). Unlike antisense RNA, iRNA is recycled by the cell's biochemical machinery to further silence gene products encoded by mRNA. This results in increased efficiency of the gene silencing. The major problems associated with iRNA include their permeability into cells and their stability, particularly in the presence of nucleases.

These problems have been addressed by the incorporation of pulmonary surface active material ("SAM"), lipid or amine based transfection agents, electroporation, viral vectors or plasmid vectors. The latter technique is particularly interesting in that the plasmid vectors cause the siRNA to adopt a "hairpin" structure and these iRNA variants have been given the name of short hairpin RNA or shRNA. These shRNA molecules have enhanced silencing capacity. Moreover, there is a body of evidence that suggests that transfection agents are not necessarily required for the siRNA molecules to enter the cell. The recent discovery of pulmonary applications of siRNA and viroids are two reported phenomena wherein naked RNA can enter the cell and silence gene products. As a matter of fact, it is well known by scientists in this field that the secondary structure of the RNA does not seem to impact its gene silencing effects.

RNA is an oligonucleotide with multiple phosphate groups. Magnesium forms very strong bonds with phosphates and so RNA-Mg complexes are likely to have the magnesium atoms bound to the phosphate groups. By combining magnesium with RNA under anhydrous conditions, a covalent bond is formed, which, theoretically, would increase the lipophilicity of that portion of the RNA molecule. Furthermore, the magnesium center can bind multiple phosphate groups, theoretically, causing the formation of the hairpin structure mentioned above. This hairpin structure would not only manifest a lipophilic residue but would also provide greater resistance to attack from nucleases, which would lead to greater stability.

Since RNA would have other phosphate groups in excess of what is bound to magnesium, that portion of the RNA molecule would retain its water solubility. This novel form of RNA would have the desired amphiphilic properties that are important for mass transfer (hydrophilicity) and absorption (lipophilicity). For further discussion on this point see the "Improved solubility" section below.

A typical process would entail combining RNA with a magnesium salt in an anhydrous solvent. A suitable solvent may be DMSO or perhaps an ionic liquid. An advantage of ionic liquids is that recovery of the magnesium-RNA complex would merely entail adding the solution to an ionic liquid miscible non-solvent such as alcohol (or in some cases supercritical $CO_2$ may work), where the desired product would precipitate out. The ionic liquid could then be recycled for the next reaction by distilling off the alcohol.

The above process would likely be applicable to any water soluble biologically active agent. Thus it is an embodiment of the invention that the biologically active agent is any saccharide, peptide or nucleotide. In a preferred embodiment of the invention the biologically active agent is a nucleotide. In a more preferred embodiment of the invention the biologically active agent is an antisense RNA, interference RNA or an aptamer. It is a preferred embodiment of the invention that the metal is selected from the main group elements. It is a further preferred embodiment of the invention that the metal is selected from the s-block main group elements. It is recognized that magnesium binds to nucleic acids more tightly than calcium, thus it is a most preferred embodiment of the invention that the metal is magnesium.

Improved Solubility/Permeability

In quantifying drug absorption it is useful to apply the term bioavailability. This is defined as the fraction (F) of the dose that reaches the systemic circulation. Thus, in the extreme cases, F=0 in drugs which are not absorbed at all in the GI tract while for drugs that are completely absorbed (and not metabolized by a first pass effect) F=1. The bioavailability can be calculated from the area under the curve (AUC) of the serum level vs. time plot. It depends on many factors and some of these factors differ between normal individuals. In terms of bioavailability, drugs have been classified into four categories according to the table below.

| Class | Solubility | Permeability | Bioavailability Expectation |
|---|---|---|---|
| I | High | High | Very high bioavailability but is rare due to the requirement for active transport |
| II | Low | High | Reasonable bioavailability if solubility problem is not too severe |
| III | High | Low | Low permeability is difficult to overcome and drugs may be shelved for this reason. |
| IV | Low | Low | Very low or no bioavailability. Drugs in this class are usually not developed any further. |

As can be seen a delicate balance between cell membrane permeability and solubility needs to be struck for a drug to become a viable candidate for further development. The reason for this is because physical properties that enhance solubility (i.e. hydrophilicity) are usually orthogonal to those properties enhancing permeability (i.e. hydrophobicity or lipophilicity).

The interaction between metals and tetracycline antibiotics has been shown to reduce the bioavailability of both the drug and the metal. As stated earlier, the bioavailability of tetracycline antibiotics are mainly influenced by the physicochemical properties of the metal complexes that prevail in the GI tract. Electric charge has the greatest impact on bioavailability since neutral species are more likely to readily absorb into the phospholipid membrane of the intestinal cells. A lipophilic metal coordinated complex should serve to allow greater bioavailability vis-à-vis metal salts of the drugs, which carry electric charges. Thus it is an embodiment of this invention that by administering lipophilic metal-antibiotic covalent complexes, physicochemical properties of the antibiotic can be controlled and, further, may prevent the metals in the GI tract to impact the dynamics of metal interaction with the drug and ultimately absorption. It is a further embodiment of this invention that the above stated principle is generally applicable to all drugs.

This technology can also be used to increase the lipophilicity of highly water soluble drugs, or the so called Class III drugs. In this case, the conversion of an ionic center, such as a phosphate or sulfate group, is converted to a covalent bond. This change in bonding between metal and ligand is known to decrease water solubility and increase organic solvent solubility or lipophilicity of the ligand.

If a drug is poorly soluble but is readily permeable one way its solubility can be enhanced is by covalently attaching water soluble entities such as amino acids or carbohydrates, to the drug. Alternatively, by forming a metal-ligand complex between the drug and an ionized metal center a new chemical entity is formed that now has inherent hydrophilicity imparted to it. It is an embodiment of this invention to bind the active agent to a transition metal or alkaline earth metal to form a new composition of matter that has improved solubility while retaining its permeability. Since the new metal ligand bond is covalent, it is preferable that the metal have additional ligands (e.g., amino acid) attached to it to counterbalance the lipophilic nature of the newly formed covalent metal center.

Due to the covalent nature the stability of the metal-active agent complex is retained up to transport to the water film coating of the brush border membrane. When the complex reaches the membrane the metal and the drug are separated by the lipids in the membrane accepting the lipophilic active agent and rejecting the hydrophilic metal. This is imparted through physicochemical action and, in contrast to the earlier methods of increasing solubilities of drugs, does not require enzymes.

Drugs are applied to the skin to elicit an effect to the 1) skin surface, 2) an effect within the stratum corneum, 3) an effect requiring deeper penetration into the epidermis and dermis or 4) a systemic effect through penetration to the vasculature. The aim of this research is to design a new transdermal drug delivery (TDD) system that will allow penetration of the drug through the epidermis or into the vasculature. The desired level of penetration will depend on the drug.

The stratum corneum provides an effective barrier and prevents water and chemicals from penetrating to the epidermis and beyond. It has been proposed that the structural organization of the lipids in the stratum corneum is an important factor in preventing fast transport of water and chemicals. This organization of lipids results in a liquid crystal morphology and penetration though this matrix is caused by destabilization of the liquid crystal through a disordering of the lipid hydrocarbon chains. This is the mechanism that has been proposed for the hydrotropes' ability to enhance penetration of topically applied drugs.

Some of the classes of chemicals that are used to enhance skin permeability include alcohols, alkyl methyl sulfoxides, pyrrolidones, surfactants (anionic, cationic and nonionic), and fatty acids and alcohols. In addition, laurocapram, urea, calcium thioglyclate, acetone and dimethyl-m-toluamide have been used to enhance skin penetration of specific bioactive reagents. Most of these drug vehicles' effect is by virtue of their hydrotropic properties. In chemical terms, many of them have a large dipole moment; that is they have a lipophilic portion and a hydrophilic portion. It is this large dipole moment which is a major contributing factor that causes these chemicals to disorder the lipids in the stratum corneum.

Many drugs do not intrinsically possess enough skin penetrative ability to be used topically. Thus, virtually every topically applied pharmaceutical requires a formulation that includes a vehicle or TDD enhancer in order to achieve the desired efficacy. Aside from the standard requirements of safety and efficacy to which all pharmaceuticals must comply, topically applied drugs need to be soluble and stable in the vehicle, the formulation must have content uniformity, the formulation must have proper viscosity and dispersion characteristics and must maximize patient compliance, which means it must not be uncomfortable to apply, have an unpleasant odor or cause skin irritation.

Most notably, the lag time for the drug's penetration into the epidermis, which relies on its ability to partition from the vehicle into the stratum corneum, has presented significant obstacles during the development of TDD formulations. Previous reports show that this lag time can be anytime between minutes to several days. Thus, a major impediment of the development of TDD systems has been these additional considerations unique to this application and, historically, the development time for transdermal pharmaceuticals has often been viewed as exorbitant.

Enhanced transdermal permeability of a drug complex according to this invention relies on the stability of the complex coupled with its amphiphilic properties. Thus it is an embodiment that the formation of a covalent metal-drug bond converts the drug into an effective hydrotrope capable of enhancing TDD of the drug itself. It is a further embodiment of the invention that, if a TDD enhancer is still required, the metal will act as an anchor for the vehicle and the entire complex will behave as a single molecular entity. The advantage with this is that drug release from the complex no longer requires differential partition coefficients between the vehicle and the lipid matrix of the epidermis.

Due to its covalent nature, the stability of the metal-active agent complex is retained should be retained during transport through the stratum corneum. When the complex is in the epidermis the metal and the drug are separated by the lipids in the membrane accepting the lipophilic active agent and rejecting the hydrophilic metal. This is imparted through physicochemical action and, in contrast to the earlier methods of increasing solubilities of drugs, does not require enzymes.

Converting a drug to a metal coordination complex also facilitates entry into the eye. It has been shown that converting sulfonamides for treating intraocular pressure (IOP) to their metal coordination complexes increased their IOP reduction effect. It is believed that this is due, in part, to the increased presence of the sulfonamide in the eye and that this, in turn, is due to the right balance between lipo- and hydrosolubility of the metal coordinated complex. Drugs to treat eye diseases can be improved by converting them into a metal coordination complex according to this invention. This is very important to treat age-related macular degeneration (AMD), where the current therapies rely on injection of the drug behind the eye. An eye drop application of a drug to treat AMD greatly improves patient compliance; coordinating the AMD drug with a metal accomplish this.

Controlling Polymorphism

Polymorphism contributes a significant portion to the variability in dosages in part due to variation in solubility. Historically speaking, an inherent physical property of organometallic compounds is that stable crystalline forms are relatively easy to prepare. Thus it is a further embodiment of this invention that polymorphism is overcome by converting the active agent into a metal complex and subjecting the complex to recrystallization processes by methods commonly known by those skilled in the art. In so doing the active moiety is "locked" into a desired polymorph.

Modulating Drug Absorption

In recent times there has been a flurry of activity to improve drugs by modulating how the drugs are delivered. Drug delivery technology spans over all forms of administration from oral to injectable to implants to skin patches. Most of these technologies make use of an encapsulation technique or bead technology wherein the active ingredient is encapsulated or "trapped" inside a polymeric sphere. This polymeric sphere can exist as a micelle, as a self assembled molecular rod or ball or a coating around the active ingredient. The drug is released by solvation or swelling from the encapsulating agent as it circulates through the blood or traverses the gut. The main advantage of modulating the delivery of the drug is to extend its release, modulate the blood levels for improved safety or enhance its absorption for improved efficacy. Thus it is an embodiment of this invention that drug-metal complex release is modulated in vivo by physicochemical action on the complex itself.

In certain cases it may be beneficial to enhance the stability of the active agent-metal complex by encapsulating the drug-metal complex within a porphine, peptide or polymeric matrix. This is particularly true if the active agent does not contain the necessary elements for forming a stable complex with a metal, such as with the primary amines or alcohols mentioned above. It is a preferred embodiment of the invention that the matrix be a porphine derivative, modified, if necessary, to allow bonding of the active agent to the metal. It is an embodiment of this invention that drug-metal complex release is modulated in vivo by physicochemical action on the porphine, peptide or polymeric matrix. It is a further preferred embodiment of this invention that the matrix be a compound found naturally in the small intestines. In yet a further preferred embodiment of this invention the porphine matrix is bilirubin or a derivative thereof.

Figure 8:
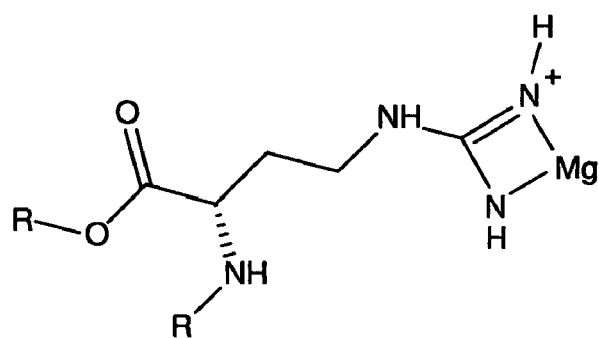
FIG. 8 illustrates a substituted arginine:magnesium complex in accordance with the present invention.

It is a further preferred embodiment of the invention that the encapsulating matrix is an amino acid or dipeptide, wherein amino acids or multiple dipeptides can be added to coordinate with or self assemble about the metal-ligand complex. Histidine is an ideal amino acid due to the strong metal binding capacity of the imidazole moiety in histidine. Arginine is another amino acid well suited for complexation with magnesium through amidinate ligation of the guanidine portion of peptide bound arginine (FIG. 8). In a related embodiment of the invention, magnesium, due to its complexing and acid neutralizing, would stabilize arginine in the stomach and increase it potency. This is good for when arginine is used as a NO source to help with COPD and related disease states.

The use of amino acids as secondary ligands on the metal is to stabilize the inner coordination sphere, create a hydrophobic shell about the inner sphere and thus preventing hydrolysis of the metal-drug bond. Thus, it is an embodiment of the invention that amino acids, dipeptides or oligopeptides act as secondary ligands or adjuvants on the metal-drug complex to stabilize the complex, particularly in aqueous systems. It is a preferred embodiment of the invention that the secondary ligand is a dipeptide. It is another preferred embodiment of the invention that the secondary ligand is an amino acid. In yet another preferred embodiment of the invention the amino acid is selected from the group histidine and arginine.

Organometallic complexes that have a free amino group (e.g. having an amino acid as part of the complex such as histidine) can initiate polymerization of an amino acid-NCA to form a polypeptide, conformationally protecting the organometallic complex. It is a further advantage of this technique to allow the amino acid NCA's to self assemble about the organometallic complex and then coacervating the polypeptide into its self assembled structure upon initiation of polymerization.

Figure 9:
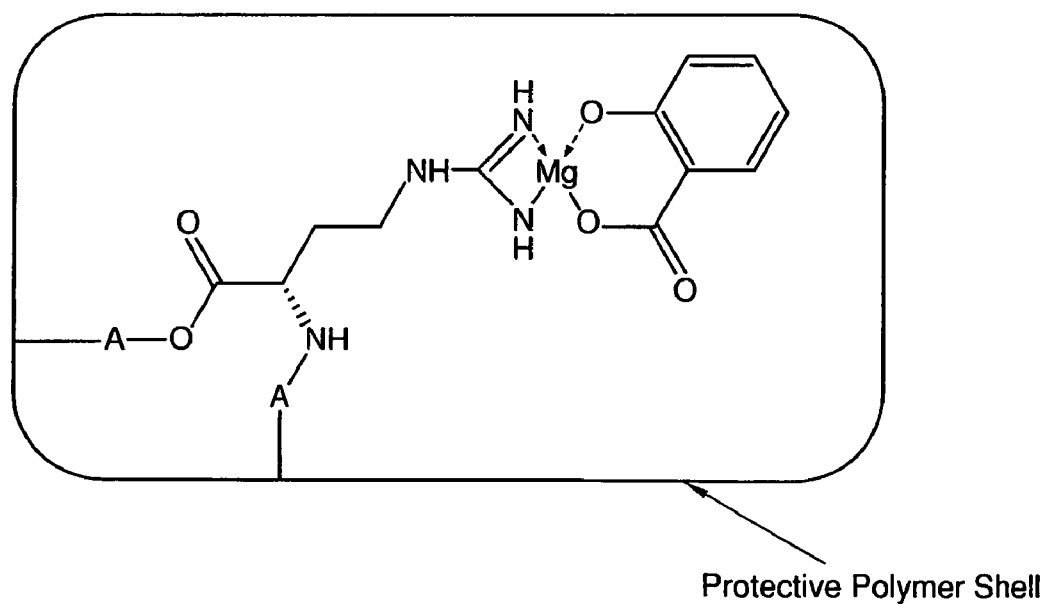
FIG. 9 illustrates salicylic acid and polymer bound arginine complexed with magnesium in the inner sphere and peptides encapsulating the ligand:metal complex in the outer sphere in accordance with the present invention.

It is an embodiment of this invention to combine the encapsulation technology with the covalent technology to form an inner sphere covalent bond between the active agent and the transition metal, thus making a new composition of matter, and then encapsulating the complex with outer sphere coordination within a polymer matrix to provide a stable complex. FIG. 9 illustrates an active agent (for structural simplicity salicylic acid is the example used), and polymer bound arginine bond to magnesium in the inner sphere and peptides encapsulating the complex in the outer sphere.

It is a further embodiment of the invention that the active agent only be released when the encapsulating matrix swells or is dissolved by water, oil, emulsions or biologic fluids such as gastric juices. It is an embodiment of the invention that the active agent cannot be released from the encapsulating matrix by virtue of the strong bond between the encapsulating agent and the active agent, such as what would occur with an antibody-antigen complex. In some cases it would be beneficial to have the release of the drug from the encapsulating agent be modulated by digestive enzymes. It is a preferred embodiment of the invention that the active agent is released from the encapsulating agent by its chemical breakdown by enzymes secreted in the intestines, within the cell membrane or circulating in the blood stream. It is preferred embodiment of the invention that the active agent is bound to aluminum, magnesium, calcium, iron, bismuth, silicon or zinc. In another most preferred embodiment of the invention the encapsulating agent is an antibody raised against the metal-ligand complex. In yet another embodiment of the invention the complex comprises an active agent-metal complex and the encapsulating agent is self-assembled from the combinations of amino acids, porphines, carbohydrates or mixtures thereof. In a most preferred embodiment of the invention the active agent-metal-encapsulating agent complex is a pharmaceutical.

In another embodiment of the invention, the coordination complex is a metal selected from all metals that can form such complexes, and the drug is selected from the group of all biologically or pharmacologically active agents. In a preferred embodiment of the invention the pharmacologically active agent requires a specific conformation for biological activity. The activity could be dependant on the active agent's ability to cross cell membranes and the coordinating metal provides the correct structure for membrane translocation of the active agent. In a preferred embodiment the pharmaceutically active agent is selected from the group consisting of small molecules, peptides, carbohydrates, DNA or RNA, the latter two being used in gene therapy, as aptamers or in anti-sense nucleotide therapeutic applications. In a preferred embodiment the metal is selected from the group consisting of aluminum, bismuth, calcium, magnesium, iron, silicon and zinc.

Bioadhesion Properties

There are a variety of ways that incorporating a magnesium or calcium ion into the molecular formula of a drug would infer bioadhesive properties to the drug. For example, it is known that magnesium and calcium are important for adhesive functions of integrins, thus it is reasonable to expect that a magnesium or calcium salt or complex of a drug in the intestinal tract would enhance bioadhesion of the drug to integrins expressed on the brush border membrane of the intestinal lining. And since bioadhesion translates into slower transit time in the gut, these complexes will confer sustained period of absorption in the gut. Therefore, it is an embodiment of this invention that sustained absorption of a drug will be enhanced by complexing the drug with magnesium or calcium. It is a further embodiment of the invention that said sustained release is conferred upon the magnesium or calcium drug complex by virtue of stronger bioadhesive properties.

Prevent Abuse of Narcotics

Narcotics are very effective analgesics but also can be very addictive. There have been many reports in the last few years describing the abuse of OxyContin by opiate addicts and recreational drug users. Typically the drug abuser will break the tablet matrix down mechanically or chemically, by adding water for example, thus making the full 12 hour dose available all at once. In addition, this type of abuse, which usually starts with oral administration, can often lead the abuser to snort or inject the concentrated narcotic.

Figure 10:
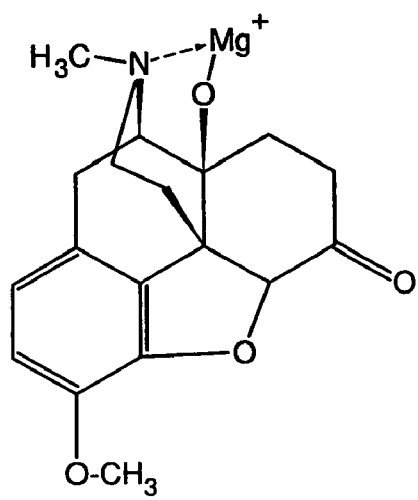
FIG. 10 illustrates a magnesium:oxycodone complex in accordance with the present invention.

Analysis of the structure of oxymorphone and oxycodone reveals that the molecules are ideal candidates for chelation with a metal. The β-hydroxyl at the 9-position and the nitrogen are positioned in such a way that complexing a metal between the two would form a highly thermodynamically favored 5-member ring. It is preferred that the 9-hydroxyl is deprotonated to form an anionic alkoxide (FIG. 10). The nitrogen's lone pair of electrons may contribute enough electron density to stabilize the metal chelate. Further stabilization can be imparted by adding secondary ligands or adjuvants to the complex in the manner of the case where salicylaldehyde stabilizes the glycine-magnesium complex. It is a further embodiment of the invention that the metal-narcotic complex is encapsulated within the matrix as described above.

Thus it is an embodiment of the invention that by virtue of the narcotic being complexed with a metal that the narcotic is released from the complex slowly through physicochemical action. This means that the narcotic is not available immediately or all at once. Furthermore, it is an embodiment of this invention that the metal-narcotic complex is unable to pass the blood brain barrier, rendering the narcotic ineffective until release from the complex has occurred. Since the kinetics of release is slow the amount of narcotic available for transport across the blood brain barrier at any one time is much less than the dose administered and so no euphoric effect is achieved. It is a further embodiment of the invention that the kinetics of narcotic release can be slowed even more by incorporating secondary ligands, encapsulating agents or a combination of both. In a preferred embodiment the metal is selected from the group consisting of aluminum, bismuth, calcium, magnesium, iron, silicon and zinc. In a more preferred embodiment of the invention the metal is selected from the main group elements. In an even more preferred embodiment of the invention the metal is selected from the s-block main group elements. In a most preferred embodiment of the invention the metal is magnesium.

Selection of Metals

Reference has been made to the preferred metals to be used in the coordination complexes. In pharmaceutical applications, the safety of the entire metal coordinated pharmaceutical needs to be considered when selecting the metal used in complexes of this invention. Although to practice this invention many metals can be used, it is a preferred embodiment of this invention that the metal be selected from a short list that would be generally regarded as safe (GRAS). One criterion for selecting the metal is to review the list of mineral supplements currently on the market and select the ones whose dosages would far exceed the dose likely to be included as a coordination complex with the drugs listed in Table 1. From the PDR for Non-prescription Drugs and Dietary Supplements a list of 7 metals (excluding alkaline metals, i.e. sodium, potassium, etc) with amounts greater than 2 mg/dose is shown in Table 2.

TABLE 2

Coordination complex candidates from the PDR for Non-prescription Drugs

| Metal | Compound | Brand Name | Amt. metal/dose |
| --- | --- | --- | --- |
| Aluminum | Aluminum Hydroxide | Maalox | 400 mg |
| Bismuth | Bismuth Subsalicylate | Pepto-Bismol | 525 mg |
| Calcium | Calcium Carbonate | Caltrate | 600 mg |
| Iron | Ferrous Fumarate | Ferretts | 106 mg |
| Magnesium | Magnesium Hydroxide | Maalox | 400 mg |
| Silicon | Sodium Metasilicate | One-A-Day | 6 mg |
| Zinc | Zinc Oxide | One-A-Day | 15 mg |

In a preferred embodiment of the invention the metal is selected from the group consisting of aluminum, bismuth, calcium, iron, magnesium, silicon and zinc. Whereas it is the embodiment of the invention that a new composition of matter is formed through the formation of a covalent bond between a pharmaceutical and any metal, including the lanthanides, actinides, the transition metals, and the main group metals (s- and p-block), it is a preferred embodiment of the invention that the metal be selected from the s-block main group elements. The reason for this is that the s-block elements are more likely to be GRAS and are more often used in OTC drug products and vitamin supplements than the transition metals or p-block main group elements (lanthanides or actinides are never used in OTC products). There are several reasons for selecting magnesium over the other s-block elements, such as calcium, which are:

1. Calcium shows larger variability with respect to coordination number with 8>7>6>9 in order of preference. Magnesium, being smaller than calcium, is almost exclusively octahedral, which simplifies the synthetic strategies and will more likely give a higher yield of a single product instead of a mixture of products.
2. Magnesium can form covalent bonds with chelating ligands more readily than the other s-block elements;
3. Magnesium forms a more stable bond with proteins and nucleic acids than calcium and thus provides enhanced stabilization of biologic pharmaceuticals.
4. Magnesium deficiency has been implicated in several disease states (e.g., cardiovascular related, migraine headaches, ADHD), and so from a prophylactic point of view magnesium may have significant benefit. For example, triptan magnesium may be an ideal candidate for this technology.
5. Calcium is absorbed in the intestines by an active transport mechanism, whereas magnesium is transported passively. Magnesium (as a salt) and Furosemide's intestinal transport were facilitated when both were co-administered orally. Thus Furosemide, a poorly absorbed drug, represents another compelling candidate for this technology.

It is a most preferred embodiment of this invention that the metal is magnesium.

Selection of Solvents

As stated earlier, the selection of solvent for the complexation reaction has an impact on the structure and stability of the metal coordinated compound. Magnesium forms strong bonds with water and the coordination sphere hydrated magnesium will have an impact on the kinetics of product formation as well as the structure and stability of the product. Because of the strong nitrogen-transition metal bond, in those cases where nitrogen containing ligands are reacted with transition metals, such as zinc, the presence of water in the reaction mixture will usually not have as strong an impact on the structure and stability of the metal coordinated product.

In some cases, depending on the ligand, the metal and the desired product water may be the solvent of choice. The majority of the products will dictate that an anhydrous organic solvent will be the best selection. Some suitable solvents include alcohol, acetone or THF. The most preferable solvent is DMSO because it is an excellent universal solvent that dissolves virtually every pharmaceutical or nutraceutical and also will dissolve most metal halides including magnesium chloride. This allows for single phase reactions. In addition, a stable metal coordinated pharmaceutical can be isolated by a process similar to coacervation, which typically will include simply adding a non-solvent to the reaction mixture.

DMSO can form complexes with metals, including magnesium, in situ, setting up the DMSO-metal complex to react with the drug ligand, thereby displacing the DMSO ligand at the metal center. DMSO can then serve as a transient protecting group in those reactions where adjuvants are to be included in the complex. This in-process reaction scheme is facilitated by the fact that the DMSO-metal complex cannot form outer coordination spheres like water does due to the lack of hydrogen bonding between the DMSO ligands. This makes the metal center easily accessible by incoming ligands. Depending on the metal coordinated complex formed, the final product may or may not retain DMSO as a ligand. If DMSO is attached to the ligand, it is unlikely that a situation will exist such that the dosing of DMSO will ever reach anywhere close to toxic levels.

It is the premise of this invention that by merely adding a metal salt to an aqueous solution of a biologically active ligand the coordination complex formed is not the same as if the combination of the reagents were done under anhydrous conditions. Furthermore, by reconstituting the dried coordination complexes in the same aqueous environment the structure of the two complexes would be different. To that end, several coordination complexes can be prepared with FDA approved pharmaceuticals, demonstrating that the complexes are stable. The products will be characterized as completely as possible and bioavailability studies will be conducted. The metal coordinated complexes can be prepared in water and organic solvents. It is expected that, in many cases, the respective products will have differences in stability, structure or biological activity.

Selection of Drugs

Complexes of almost any drug that can form a stable complex with a metal is enabled by this invention. The drugs selected for examples below represent a cross section of chemical and therapeutic classes as shown in Table 2.

TABLE 3

Drugs selected as examples in the invention

| Drug | Therapeutic Class | Chemical Class |
|---|---|---|
| Triidothyronine | Hypothyroid drug | Amino Acid |
| Minocycline | Antibiotic | β-diketone |
| Tetracycline | Antibiotic | β-diketone |
| Hydrochlorothiazide | Diuretic | Sulfonamide |
| Metformin | Diabetes drug | Biguanide |
| Acycloguanosine | Antiviral | Ureide |
| iRNA | Gene therapy | Oligonucleotide |

Small Molecule Discussions

Synthesis

Other drug-magnesium complexes that may be important include Triptan-Mg due to the importance of magnesium for headache relief and Oxycodone-Mg because of the importance of abuse resistant narcotics.

Typically an anhydrous metal halide (iodide, bromide or chloride) is added to a mixture of the drug and KO$^t$Bu in $^t$BuOH/DMSO. Alternatively, the metal halide can be added to the drug plus a solution of a tertiary amine (e.g. triethylamine) in DMSO. Yet another option is where the metal halide can be added to the drug plus KH in THF. The metals of choice are magnesium and zinc and the halide of choice is chloride. Zinc chloride is soluble in DMSO, acetone or ethanol and are the solvents of choice for zinc complexation, particularly with nitrogen containing ligands.

The product is isolated by precipitation, is separated from the liquid by suction filtration or centrifugation, washed and then dried under high vacuum to remove the last traces of moisture. The drug:metal complex may form a hydrate and all of the water may not be removable under high vacuum. Alternatively, the added water may not displace the remaining DMSO ligands on the metal formed in situ. Consequently, the product may be a drug:metal:DMSO complex.

Certain drugs, where their dissociation constants are high when bound to magnesium, favor complexation with DMSO. Formation of ternary complexes in situ would further stabilize the complexes and would retain their molecular integrity during the process of absorption after oral administration. It is for this reason that for most drugs when reacted with magnesium halide, DMSO is the solvent of choice.

As a comparator for the complexation reactions in the examples (excluding the acycloguanosine-Mg and T3-Zn examples), the reaction is repeated except water is included in the reaction medium as described in the examples below. The reaction is worked up and dried as before.

Figure 11:
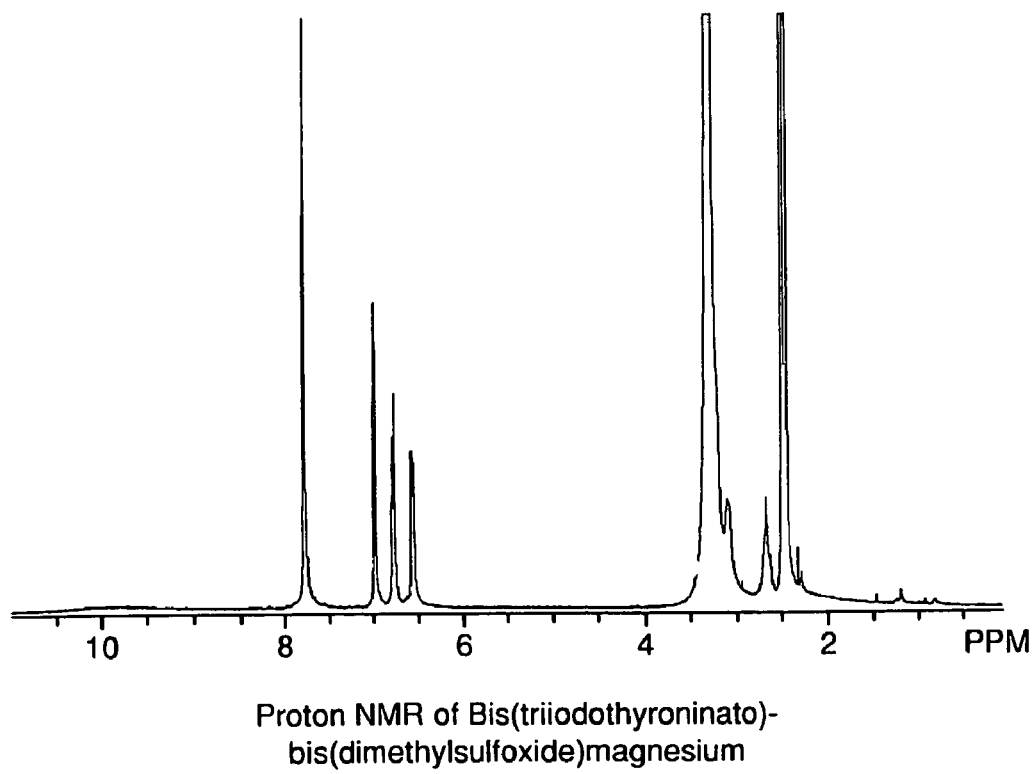
FIG. 11 illustrates the proton NMR of Bis(triiodothyroninato)-bis(dimethylsulfoxide)magnesium in accordance with the present invention.

Adding water to the T3-Mg complexation reaction clearly had an impact on the isolated product. The T3-Mg compounds prepared in DMSO alone, showed line broadening in the aliphatic region only, with sharp aromatic peaks, in its $^1$H NMR spectrum (FIG. 11).

Figure 12:
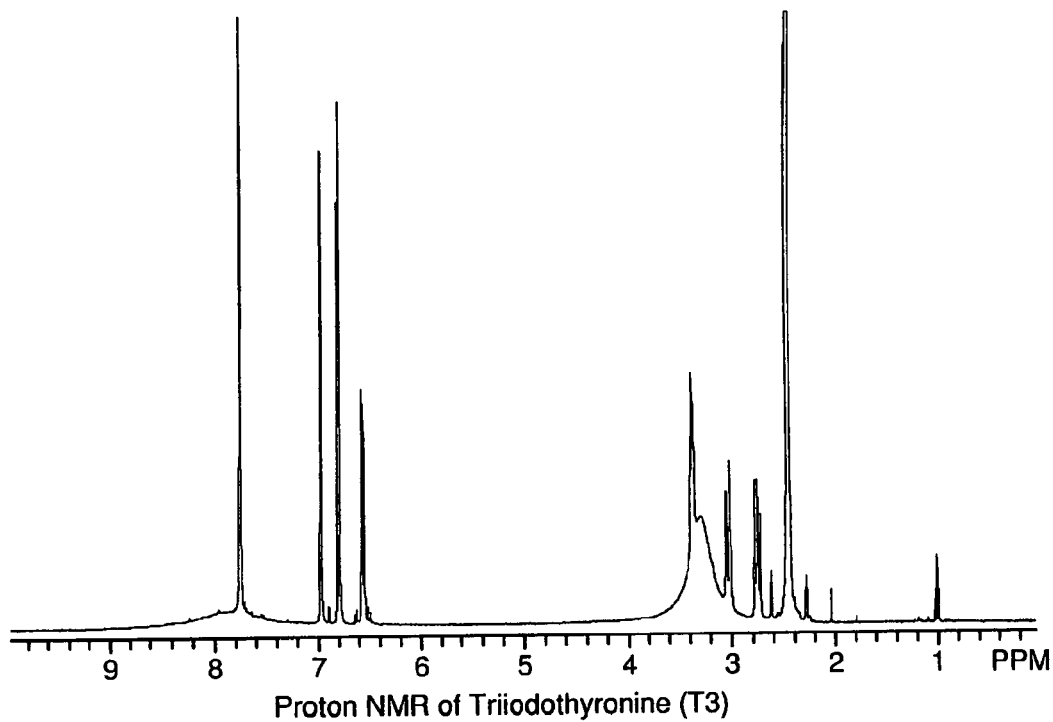
FIG. 12 illustrates the proton NMR of Triiodothyronine (T3) in accordance with the prior art.

The $^1$H NMR of T3, which shows the sharp peaks in the aliphatic region, is shown in FIG. 12. By comparison, the $^1$H NMR of the T3-Mg product prepared in the presence of water revealed extensive line broadening throughout the $^1$H NMR spectra. Furthermore, the magnesium content (1.62%) of the anhydrously prepared T3-Mg product very closely matched that of bis(triiodothyroninato)-bis(dimethylsulfoxide)-magnesium. In contrast, the T3-Mg complex prepared in the presence of water had a magnesium content of only 0.96%. It also had 0.23% potassium in it, whereas no potassium was detected in the bis(triiodothyroninato)-bis(dimethylsulfoxide)-magnesium product.

Tetracycline has β-diketone and β-ketophenol functionalities and will form stable complexes with magnesium. Adding water to the reaction in DMSO has very little effect on the solubility, the $^1$H NMR spectra or the metal content of the respective products. In fact the $^1$H NMR spectrum of the product isolated from a reaction done in water alone does not differ significantly from the product isolated from DMSO alone or in a 5:1 DMSO:water mixture. There is a trend of lower magnesium content with higher water content in the reaction solvent, but that may be due, primarily, to extent of hydration in the product.

Since zinc forms a very stable bond with nitrogen containing compounds, water does not interfere with complexation between zinc and the ligand but may impact the complex structure. The product resulting from reacting a metal and a drug in anhydrous DMSO typically yielded well characterized coordination complexes. For those compounds that were either not well defined structurally (i.e. HCTZ-Zinc) or were somewhat unstable (i.e., dimethylbiguanide-zinc complex), a zinc coordination complex was isolable and was, at least partially, characterized. The same complexes prepared in the presence of water, had higher solubility in polar solvents. The difference in solubilities of the products from the respective methods of preparation clearly established a difference in the products themselves. It is believed that the zinc products prepared in aqueous solvent systems produced ionic salts, outer coordination complexes, hydrated complexes or combinations thereof. This appeared to be the case in the dimethylbiguanide-zinc complex prepared in 5:1 DMSO:water mixture, where the $^1$H NMR spectrum revealed resonances at 2.85 and 2.80 ppm, which correspond to the N-methyl groups and indicate free (or ionic) and complexed dimethylbiguanide, respectively.

Characterization

Each product synthesized were characterized by NMR, MS (either TOF or FAB) and ICP. The NMR spectrum confirms the integrity of the sample and shows that a metal is complexed by the presence of line broadening, peak shifts or multiple resonances.

Metal content for most of the complexes prepared in anhydrous DMSO were consistent with a complex of two drugs bound to a metal. In addition, the metal content remained constant from batch to batch. The complexes of Dimethylbiguanide had variable metal content depending on the method of isolation and never had consistent drug:metal ratios. The metal content was determined by the ICP analysis and based on that data, in conjunction with the NMR and MS, the ratio of drug to metal can be calculated.

Figure 13:
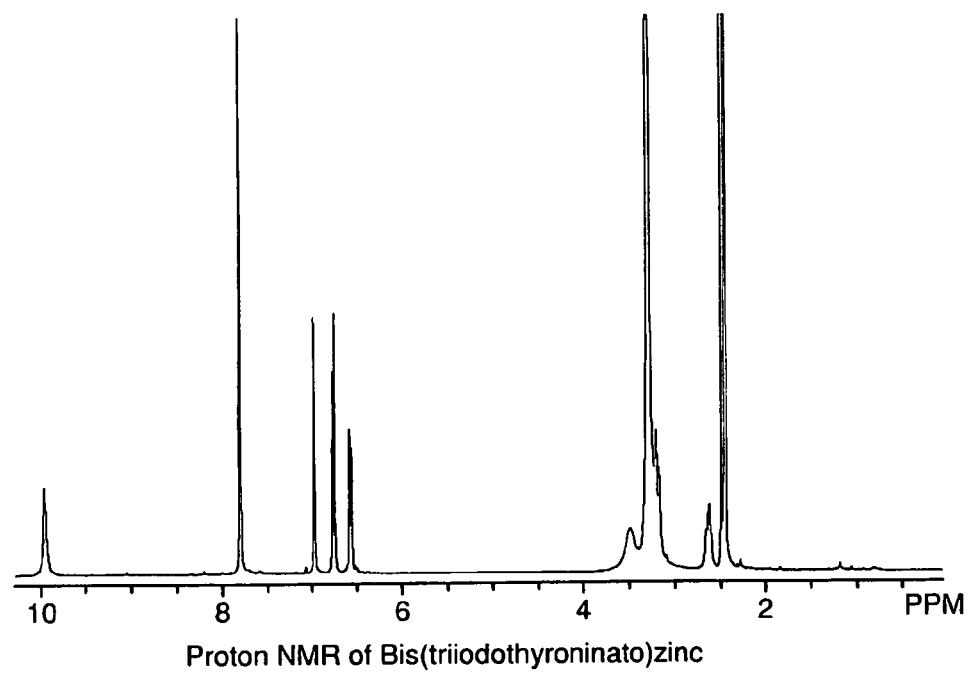
FIG. 13 illustrates the proton NMR of Bis(triiodothyroninato)zinc in accordance with the present invention.

The $^1$H NMR spectra of the T3 complexes showed some line broadening and upfield shifting in the aliphatic region indicative of complex formation with the amino acid portion of the molecule. This can be seen by comparing the region between 2.5 ppm and 3.5 ppm in the $^1$H NMR spectra of, bis(T3)bis(DMSO)Mg, T3, free acid and bis(T3)Zn, which are shown in FIGS. 11, 12 and 13, respectively.

Figure 14:
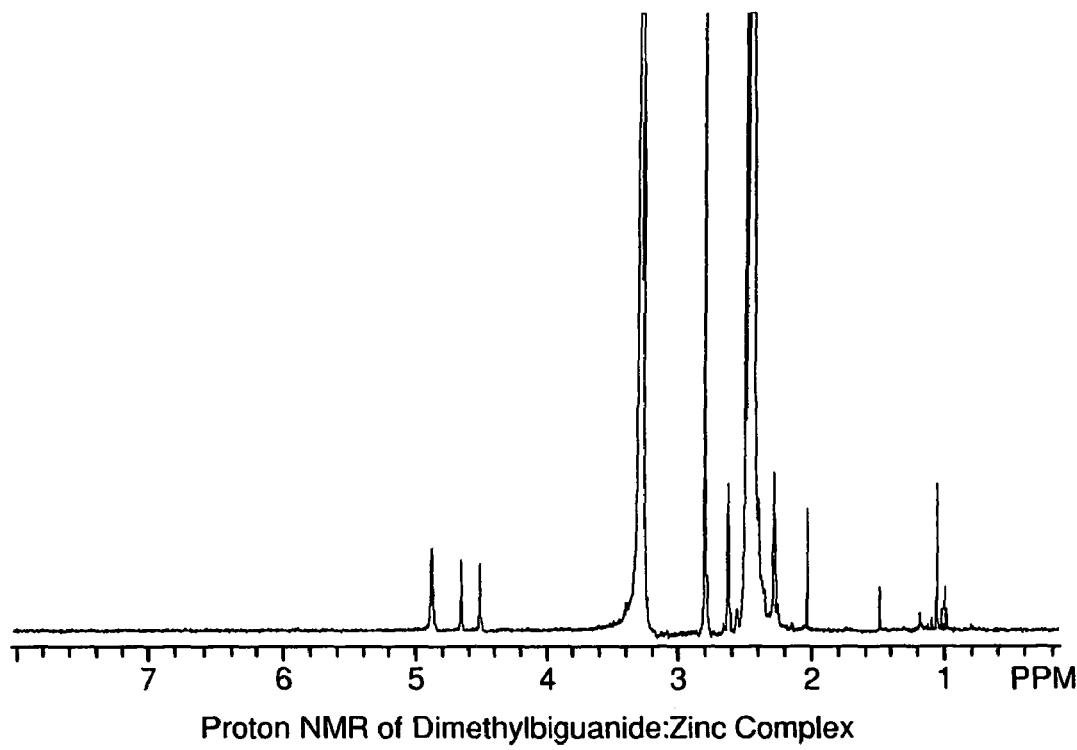
FIG. 14 illustrates the proton NMR of Dimethylbiguanide:Zinc complex in accordance with the present invention.
Figure 15:
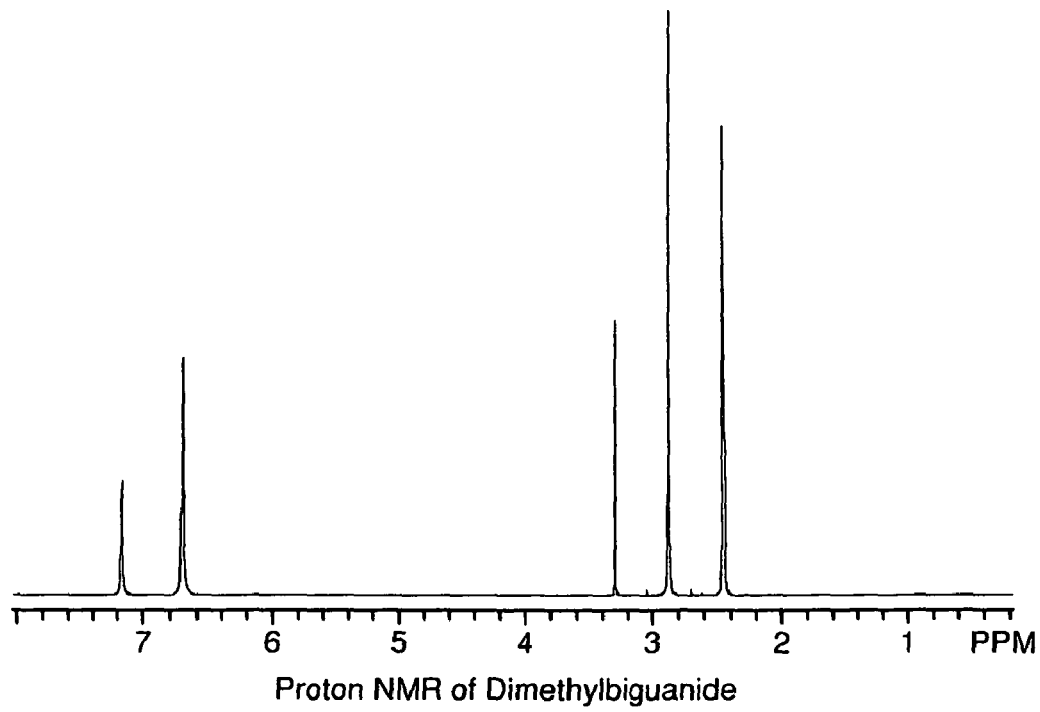
FIG. 15 illustrates the proton NMR of Dimethylbiguanide in accordance with the prior art.

The $^1$H NMR spectrum of the dimethylbiguanide complexes showed large upfield shifts of the —NH resonances indicative of complex formation with the nitrogen atoms. In addition, a 0.05 ppm upfield shift of N-dimethyl groups was observed in the dimethylbiguanide-zinc complex spectrum (FIG. 14) relative to the spectrum of dimethylbiguanide (FIG. 15)

Figure 16:
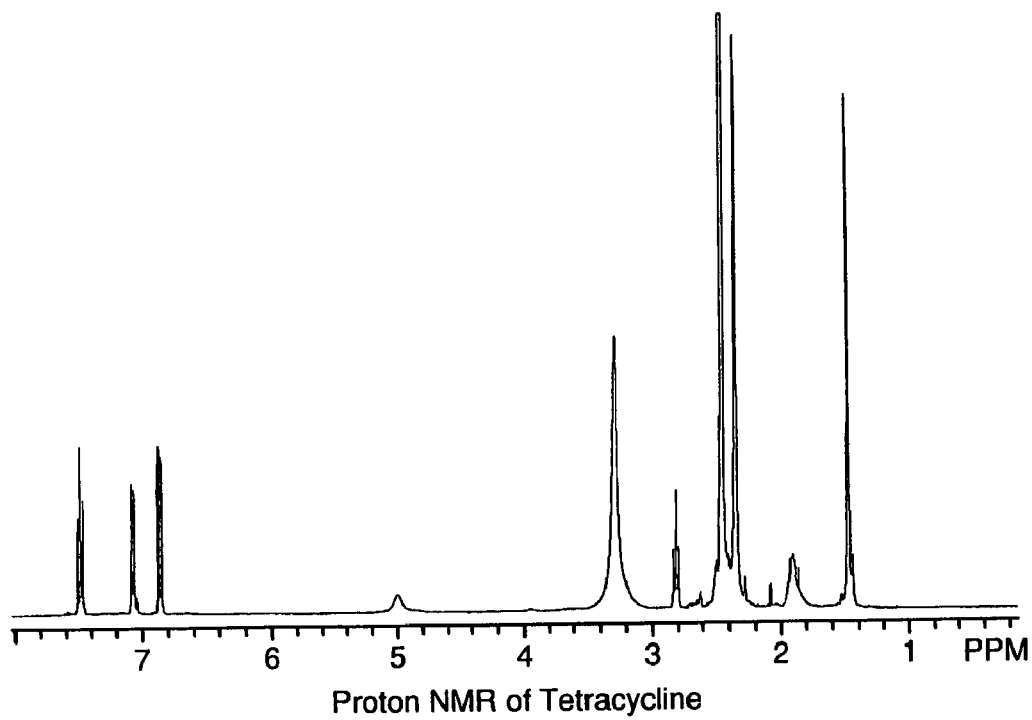
FIG. 16 illustrates the proton NMR of Tetracycline in accordance with the prior art.
Figure 17:
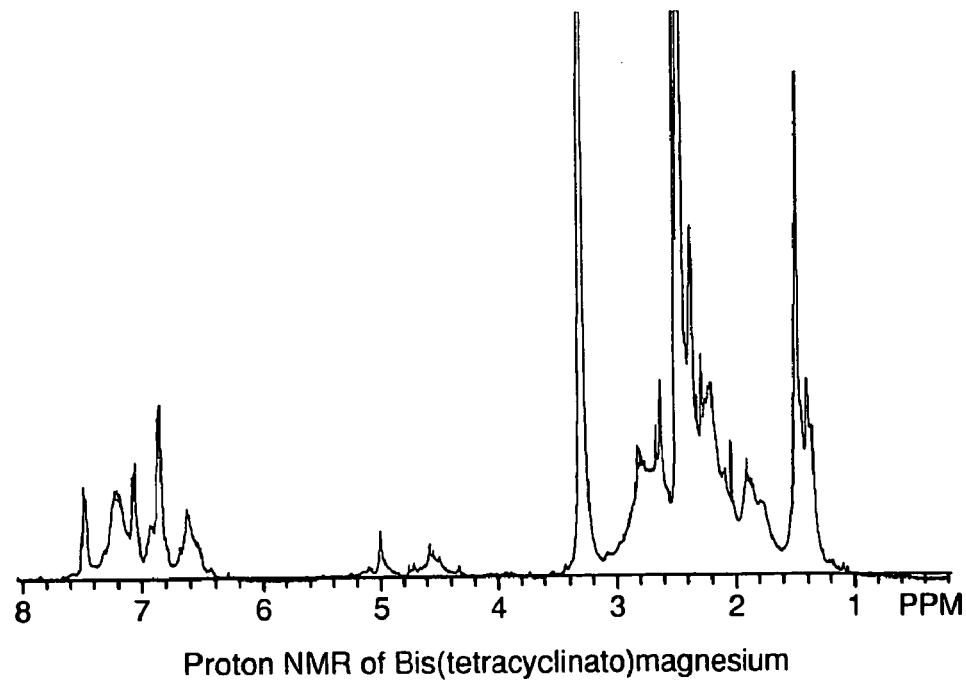
FIG. 17 illustrates the proton NMR of Bis(tetracyclinato) magnesium in accordance with the present invention.
Figure 18:
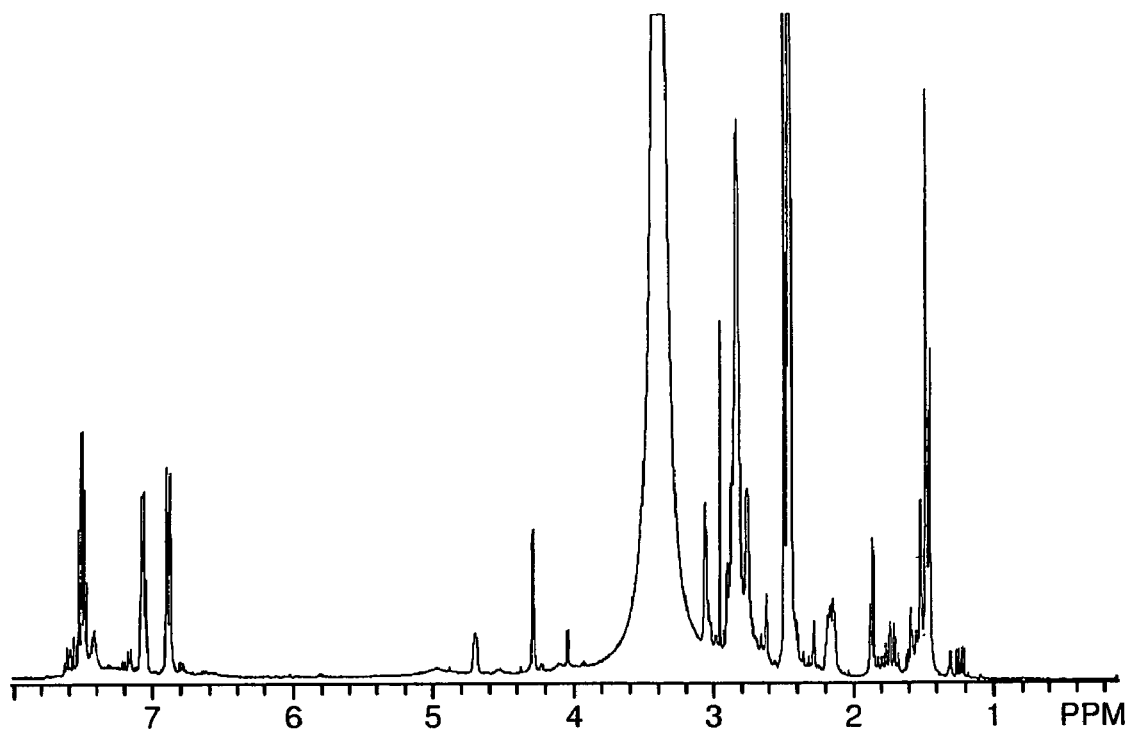
FIG. 18 illustrates the proton NMR of Tetracycline-magnesium complex with 1N HCl added in accordance with the present invention.
Figure 19:
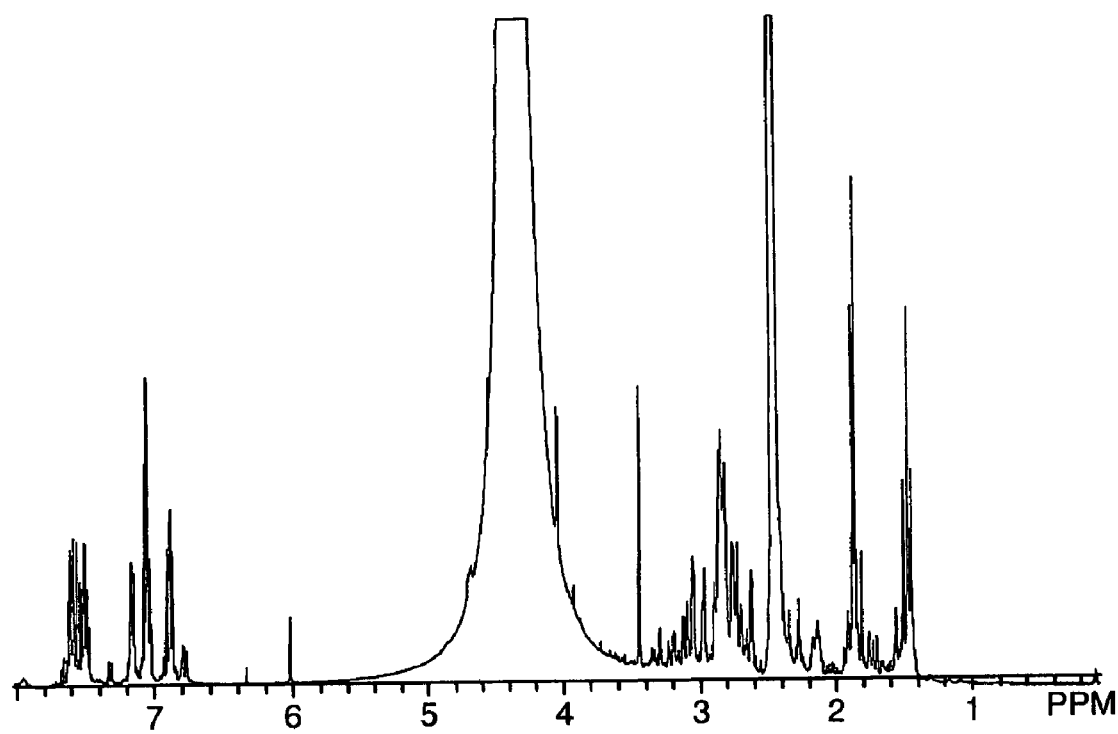
FIG. 19 illustrates the proton NMR of Tetracycline with 1N HCl added in accordance with the present invention.

The $^1$H NMR spectrum of the minocycline and tetracycline complexes resembled polymeric structures with very large line broadening and manifestation of many new resonances throughout the entire spectrum. To demonstrate that these spectra were due to dynamic isomeric mixtures and not decomposition or polymerization, 12 N HCl was added to the NMR samples of tetracycline and its magnesium complex and the spectra retaken. FIGS. 16-18 show the $^1$H NMR spectra of Tetracycline, bis(tetracyclinato)magnesium and the complex with HCl added, respectively. As can be seen in the spectra series the magnesium complex reverted back to the reference tetracycline compound. Interestingly, when HCl was added to tetracycline, a considerable amount of decomposition could be seen in the aromatic region of the NMR spectrum (FIG. 19), the magnitude of which was not seen in the commensurate spectra of the tetracycline-magnesium complex. This indicates an acid protective effect imparted by complexation with magnesium and could become an important attribute of this technology for those drugs that are unstable in acid environments, such as in the stomach.

Figure 20:
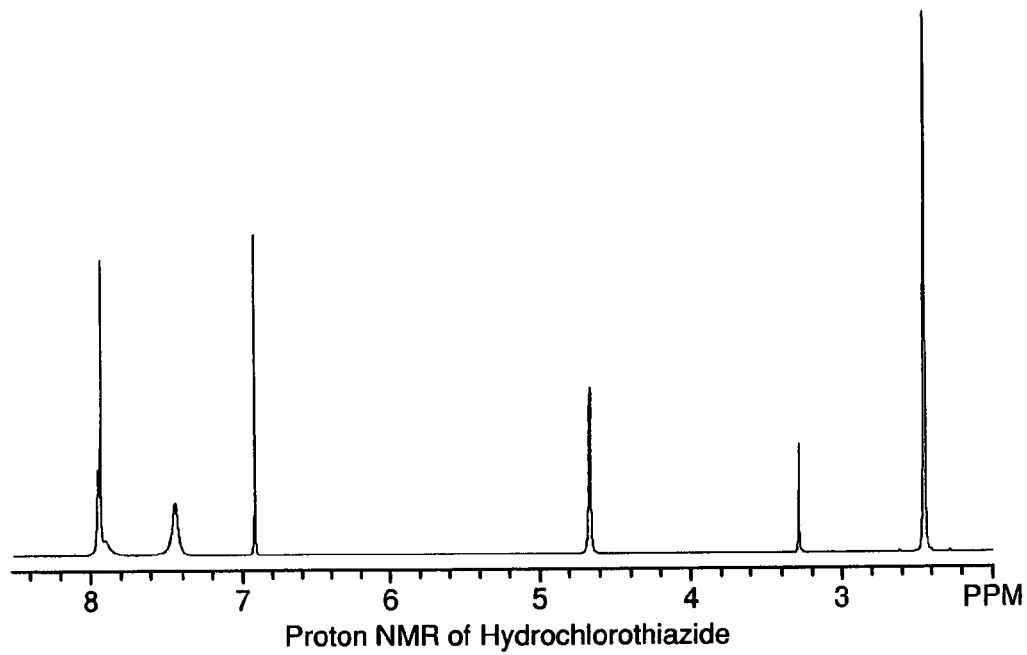
FIG. 20 illustrates the proton NMR of Hydrochlorothiazide in accordance with the prior art.
Figure 21:
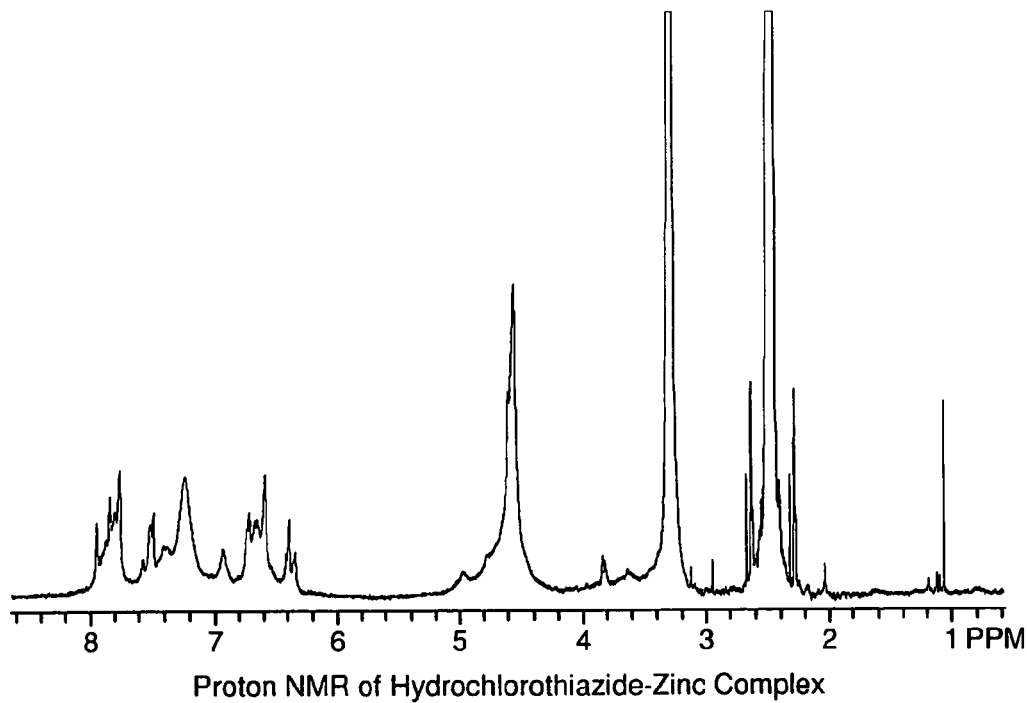
FIG. 21 illustrates the proton NMR of Hydrochlorothiazide-Zinc complex in accordance with the present invention.
Figure 22:
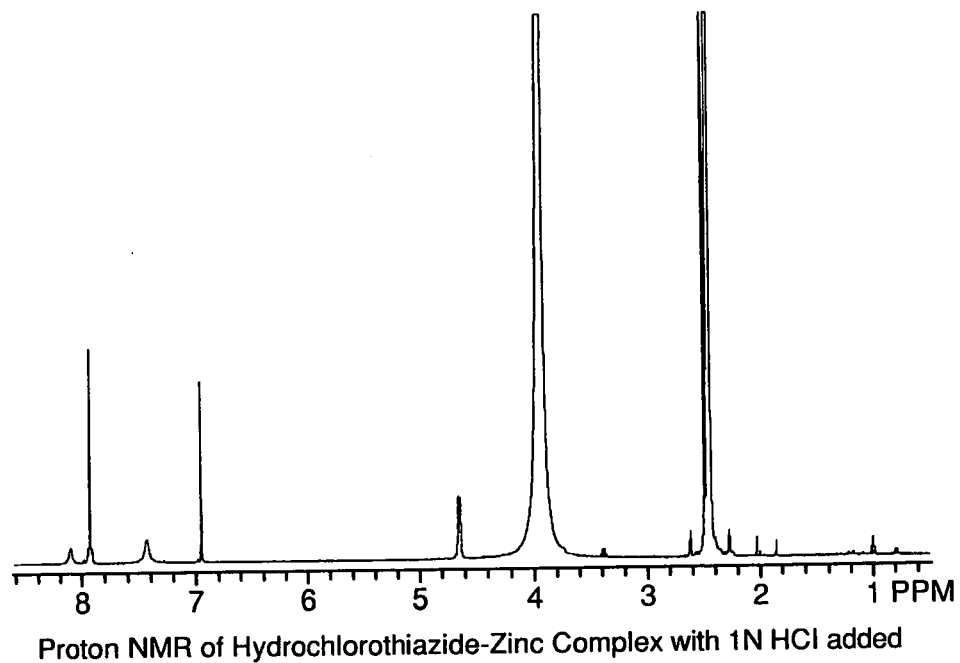
FIG. 22 illustrates the proton NMR of Hydrochlorothiazide-Zinc complex with 1N HCl added in accordance with the present invention.

The $^1$H NMR spectrum of the hydrochlorothiazide complexes also resembled polymeric structures with the same kind of line broadening and new nondescript resonances seen in the spectra of the antibiotic-metal complexes. FIGS. 20-22 show the $^1$H NMR spectrum of hydrochlorothiazide, hydrochlorothiazide-zinc complex and the complex with HCl added, respectively. As can be seen the line broadening was reverted back to the sharp resonances observed in the reference drug. This proves that the line broadening and additional resonances observed in the $^1$H NMR spectrum of the respective complexes were due to multiple stereochemical and geometric isomers of the complex in solution. Moderately slow interchange between the isomers in solution could also contribute to the line broadening observed.

Figure 23:
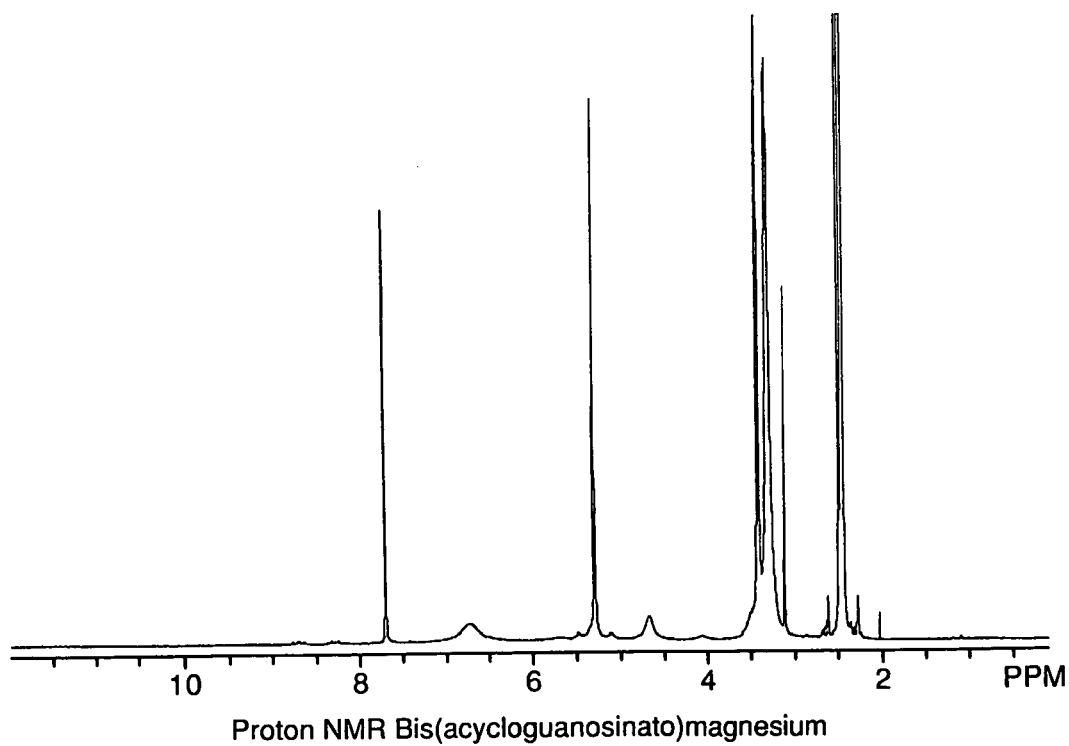
FIG. 23 illustrates the proton NMR Bis(acycloguanosinato)magnesium in accordance with the present invention.

Spectral data on the acycloguanosine-magnesium complex data showed that a complex was formed. Comparison of the $^1$H NMR spectra of acycloguanosine with that of its magnesium complex (FIG. 23) suggested that the complexation site on acycloguanosine was the amide oxygen and the imidazole nitrogen; the resonance at 10.6 ppm, which is missing in the NMR spectrum of the complex, is assigned to the amide proton.

The mass spectrum revealing a significant presence of the coordination complex is an important indicator of the stability of the complex. Thus, molecular ions were found for bis(T3)Mg, bis(T3)Zn, bis(minocyclinato)Mg, bis(tetracyclinato)Mg, and bis(acycloguanosinato)Mg. Two molecular ions with zinc isotope patterns were observed in the MALDI spectrum of hydrochlorothiazide-zinc complex. It is not known, at this time, a structure corresponding to those masses. Dimethylbiguanide-zinc complex did not have a zinc containing molecular ion in its MALDI spectrum. This is believed to be due to the compound's instability.

FTIR studies may be used to determine whether, for a particular complex that has been found, the ligand bonding atom and if the complex is coordinated with DMSO, water, or not solvated at all.

Stability

Equilibrium constants for the coordination complexes made have been estimated from literature precedents of similar compounds. For example, the equilibrium constant, log $K_{eq}$ for T3-Zn is estimated to be between 4 and 5 based on another amino acid zinc complex, phenylalanine-zinc. Likewise, the log $K_{eq}$ for dimethylbiguanide-zinc is estimated to be between 5 and 7. The log $K_{eq}$ for hydrochlorothiazide-zinc is difficult to estimate from literature values. Stability constants for tetracycline-magnesium in water at various pH values have been reported and the expected log $K_{eq}$ for tetracycline-magnesium is between 4 and 5. The log $K_{eq}$ for acycloguanosine-magnesium is estimated to be 1.6. The log $K_{eq}$ for T3-Mg is difficult to estimate due to the lack of a good comparator but the log $K_{eq}$ for glycine, which like T3 is also an amino acid, is 1.34. Due to T3's much greater hydrophobicity relative to glycine, the log $K_{eq}$ for T3-Mg is expected to be much larger than 1.34.

Another indicator of drug-metal or drug-metal-adjuvant stability is their binding constants, which is related to $K_{eq}$ but further shows the stepwise stability for multi-dentate ligands. The cumulative binding constant, $\beta_n$, for the maximum binding between the metal and the ligand is given by Equation 4.

$$\beta_n = \frac{[ML_n]}{[M][L]^n} = \sum_{i=1}^{n} K_i \qquad \text{Equation 4}$$

This difference can be seen in the measured log $K_{eq}$ for phenylalanine-zinc and its approximated $\beta_2$ value of 8.5. This $\beta_2$ value may also more closely reflect the stability of the T3-Zn complex.

There are several ways in which binding constants of metal-drug complexes in different environments can be estimated. Optical absorption spectroscopy, NMR spectroscopy, mass spectrometry, reaction kinetics, potentiometry and chromatography are several such methods.

Partition Coefficient and Distribution Coefficient

The partition coefficient is a constant and is defined as the ratio of concentration of a neutral compound in aqueous phase to the concentration in an immiscible organic phase, as shown in Equation 5.

$$\text{Partition Coefficient}, P=[\text{Organic}]/[\text{Aqueous}] \qquad \text{Equation 5}$$

In practice the Log P, defined in Equation 6, will vary according to the conditions under which it is measured especially pH since at a low pH bases will be ionized and at a high pH acids will be ionized.

$$\text{Log } P = \log 10 \text{ (Partition Coefficient)} \qquad \text{Equation 6}$$

Thus, a Log P=1 means 10:1 Organic:Aqueous, a Log P=0 means 1:1 Organic:Aqueous and a Log P=−1 means 1:10 Organic:Aqueous.

Naturally, ionized compounds will partition preferentially into the aqueous phase, thereby lowering their log P. For neutral molecules that are bases they will remain neutral when the pH is greater than 2 units above its pKa and for neutral acids when the pH is 2 units below its pKa.

The choice of partitioning solvent will also have an impact on log P. Most log P measurements will use the octanol:water system. Ion pairing effects impact the log P measurements and should be accounted for, especially with metal coordinated compounds such as those embodied in this invention.

In terms of pharmaceutical applications the following guidelines have been used in determining the method of administration, formulation and dosage forms:

Low Log P (below 0) Injectable
Medium (0-3) Oral
High (3-4) Transdermal
Very High (4-7) Toxic build up in fatty tissues And within the realm of orally administered drugs these guidelines have been used;

1. For optimum CNS penetration, Log P=2+/−0.7 (Hansch rules)
2. For optimum oral absorption, Log P=1.8
3. For optimum intestinal absorption, Log P=1.35
4. For optimum colonic absorption, Log P=1.32
5. For optimum sub lingual absorption, Log P=5.5
6. For optimum Percutaneous penetration, Log P=2.6 (& low mw)

The distribution coefficient (D) is the ratio of unionized compound in the organic phase to the total amount of compound in the aqueous phase given by Equation 7.

$$D=[\text{Unionised}](o)/[\text{Unionised}](aq)+[\text{Ionised}](aq) \qquad \text{Equation 7}$$

Log D is the log distribution coefficient at a particular pH (Equation 8). This is not constant and will vary according to the protogenic nature of the molecule. Log D at pH 7.4 is often quoted to give an indication of the lipophilicity of a drug at the pH of blood plasma.

$$\text{Log } D = \log_{10} \text{ (Distribution Coefficient)} \qquad \text{Equation 8}$$

Log D is related to Log P and the pKa by the following equations:

$$\text{Log } D_{(pH)} = \log P - \log[1+10^{(pH-pKa)}] \text{ for acids} \qquad \text{Equation 9}$$

$$\text{Log } D_{(pH)} = \log P - \log[1+10^{(pKa-pH)}] \text{ for bases} \qquad \text{Equation 10}$$

So, when the pH is adjusted such that ionization is minimized, the log D will be nearly equivalent to the log P. Under those conditions, then, log D is a reliable indicator of the bioavailability of a drug in a particular application. In terms of a metal coordinated drug, increases in log D of the drug-metal complex relative to the reference drug will not only indicate an increase in lipophilicity but will also demonstrate its stability in water, as well. The log D's at pH 7.4 for tetracycline, bis(tetracyclinato)magnesium, triiodothyronine and bis(triiodothyroninato)zinc were determined and are shown in Table 4 along with their pKa's.

TABLE 4 pKa and Log D for selected reference drugs and their metal coordination complexes.

| Compound | Method | pKa | Log $D_{7.4}$ |
|---|---|---|---|
| Tetracycline | DPAS | 8.95, 7.04, 3.34 | −1.2 |
| Bis(tetracyclinato)magnesium | DPAS | 8.33, 7.17, 3.36 | 0.01 |
| Triiodothyronine | Potentiometric | 8.41, 8.07 | 2.80 |
| Bis(triiodothyroninato)zinc | Potentiometric | 6.66, 6.42 | 3.43 |

DPAS = Dip Probe Absorption Spectroscopy

These results run counter to what the prior art teaches; that is combining the anion of a neutral compound with a metal salt should produce a compound with less lipophilicity and a reduced log D. Perhaps more interestingly, by application of the technology in this invention, tetracycline was theoretically transformed from an injectable drug (log D<0) to an oral drug (log D>0) and T3 was transformed from an oral drug (log D<3) to a transdermal drug (log D>3). This latter manifestation has important implications in increasing the safety of T3 products by administering the drug in a slow release transdermal depot.

Bioavailability Studies

Overview: A preliminary study in a rat model to observe the effects that coordinating a metal with a drug will have on the absorbance of the reference drug was conducted. The reference drug selected for this particularly study was triiodothyronine (T3), which is the active ingredient in Cytomel and Thyrolar. Both Cytomel and Thyrolar are currently used to treat hypothyroidism. Cytomel has also been indicated in the treatment of certain psychological disorders.

Study Design: T3-Zinc and T3-Magnesium were tested for bioavailability, relative to the reference drug over a 5 hour time period. The three compounds were formulated, separately, into gelatin capsules, with a total dose of 108±12 µg/kg administered. In order to avoid acid degradation of the test compounds in the rat stomach, metal oxides were added to the formulation. Another T3 control was included, where zinc oxide was added to T3, free acid. Each of the formulated gelatin capsules were orally administered directly to the esophagus of respective rats and blood samples were collected at pre-dosing and at 0.5, 1, 2, 2.5, 5 hours after dosing. Serum triiodothyronine levels were analyzed by an independent laboratory, using an industry standard assay method.

Results: The data shown in the FIG. 30 reveal that all four drug formulations were readily absorbed by the rat, with a rapid rise in serum T3 levels up to the 2.5 hour time point and a general leveling off in the metal coordinated T3 fed rats after that. The T3, free acid fed rats indicated that the serum T3 levels may still be rising at the 5 hour time point. The rats that were administered metal complexed T3 and T3 with zinc oxide added had an increase in serum T3 blood levels that were approximately 65-85% greater that of T3, free acid at the 5 hour time point.

Conclusions: The data clearly indicate that complexing a metal with T3 increased the absorbance of orally administered T3 nearly two fold over T3 alone. It is believed that the T3, free acid complexed with the zinc oxide prior to absorption of T3 in the animals fed the formulation of T3 and zinc oxide.

This study represents a significant advance in drug delivery technology and that coordinating metals with pharmaceuticals can be applied to and improve the performance of drugs with bioavailability limitations.

Large Molecule Protocols

Synthesis

Double stranded iRNA of a defined size were prepared according to the standard protocol described in the Examples section. The iRNA was then reacted with magnesium or zinc under anhydrous conditions or in the presence of water as described in the Examples section.

The biological activity of iRNA can be modulated in various ways by complexing it with other metals such as calcium, zinc, cobalt and manganese. In addition, combinations of multiple metals, such as including Cu or $Ag^{33}$ to facilitate binding of the purine/pyrimidine groups along with the phosphate groups can improve the transfection efficiency and stability of iRNA.

Characterization

The metal:RNA products were tested for changes in ionic/covalent behavior using Isoelectric focusing (IEF) gel following the standard protocol described in the Examples section. The advantage of the IEF gel is that it provides an inexpensive tool by which to monitor changes in the charge distribution on the target RNA molecule. Data from the IEF studies were represented as ΔpKa for each iRNA complex prepared.

Conclusion of IEF Experiments

Figure 31:
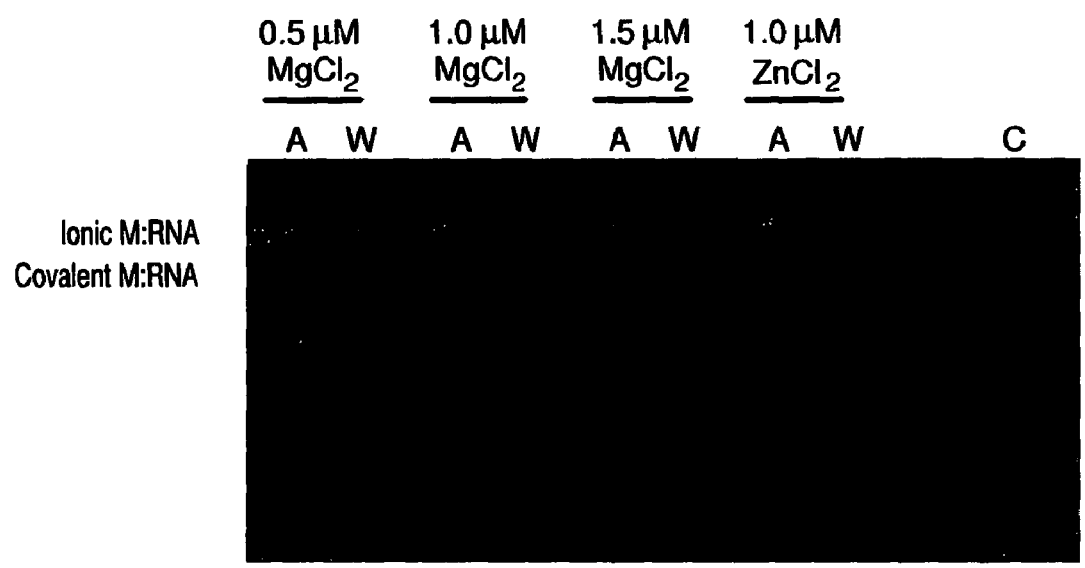
FIG. 31 illustrates the IEF profiles of magnesium and zinc iRNA complexes in accordance with the present invention. The rows labeled "A" refer to complexes prepared in anhydrous conditions. The rows labeled "W" refer to complexes prepared in water.

The presence of an RNA molecule from the anhydrous DMSO reactions with a different isoelectric point (pKa) indicates the presence a new RNA molecule (FIG. 31). Since this is not due to RNA degradation means that the new RNA molecule is a stable complex between the metal (magnesium or zinc) and RNA. In addition, because its pKa is lower than the native RNA supports the formation of a covalent bond between the metal and RNA.

EXAMPLES

FTIR Analysis of DMSO-Magnesium Complex

In order to determine which atom of DMSO binds to magnesium and FTIR spectrum was collected of a DMSO-magnesium complex. The FTIR spectrum showed an extra stretch at 954 $cm^{-1}$, which is indicative of an S=O—Mg stretch. FTIR of T3 complexes were examined for the presence of S=O—Mg, C=O and N—H stretches.

Preparation of Bis(triiodothyroninato)-bis(dimethylsulfoxide)magnesium.

Figure 24:
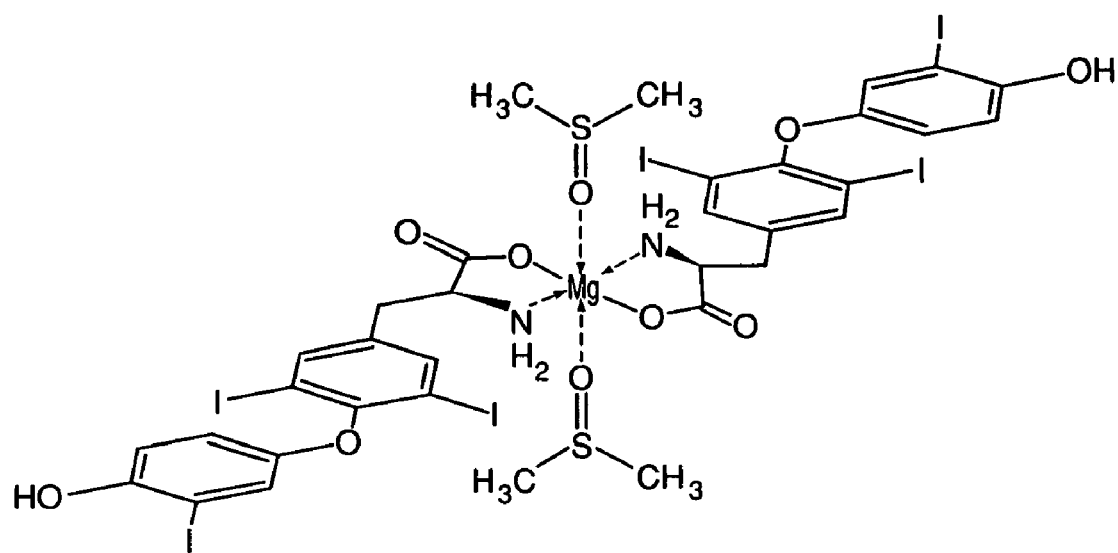
FIG. 24 illustrates the structure of Bis(triiodothyroninato)-bis(dimethylsulfoxide)magnesium in accordance with the present invention.

Triiodothyronine or T3 (218 mg) was dissolved in 4 mL of anhydrous DMSO, after which 0.34 mL of 1 M potassium t-butoxide in t-butanol was added and the solution stirred for 10 minutes. Magnesium chloride (16 mg) was added and the solution stirred overnight. The solution was poured into 10 mL of deionized water to precipitate the product, which was suction filtered and air dried. After an overnight drying under high vacuum the yield was 164 mg of a light beige powder. The product structure was characterized by $^1$H NMR, FAB-MS and ICP. $^1$H NMR (DMSO): δ 7.83 (s), 7.05 (d), 6.82 (d), 6.62 (dd), 3.26 (bm), 3.15 (bd), 2.71 (bm), 2.54 (s). The presence of the broad multiplets in the side chain region indicates that as the site for magnesium binding (see FIG. 11). FAB-MS: Molecular ion at 1325 indicative of bis(triiodothyroninato)magnesium (after loss of DMSO ligands). FTIR (neat): $cm^{-1}$ 1596 (C=O stretch), 1014 (S=O stretch), 949 (S=O—Mg stretch); absence of N—H stretch at 1633. Magnesium analysis (ICP): Expected 1.68%; Found 1.62%. This confirms the structure as shown in FIG. 24 and is about 96% pure, where most of the contamination is probably due to water as seen in the $^1$H NMR spectrum.

Preparation of Bis(triiodothyroninato)zinc.

Figure 25:
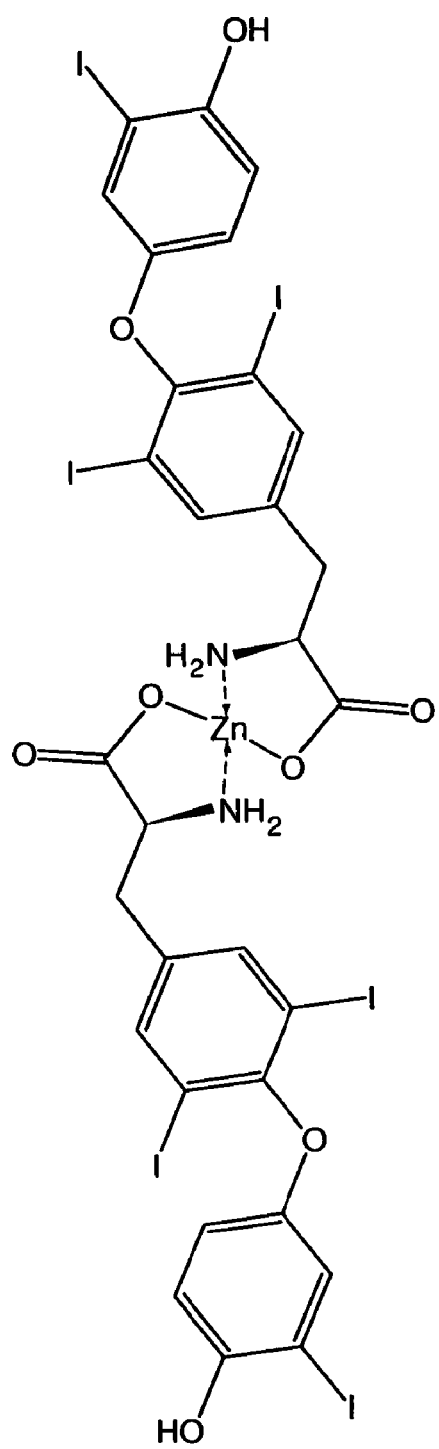
FIG. 25 illustrates the structure of Bis(triiodothyroninato) zinc in accordance with the present invention.

Triiodothyronine or T3 (192 mg) was dissolved in 4 mL of anhydrous DMSO, after which 0.30 mL of 1 M potassium t-butoxide in t-butanol was added and the solution stirred for 10 minutes. Zinc chloride in diethyl ether (0.16 mL of 1M solution) was added and the solution stirred overnight. The solution was poured into 10 mL of deionized water to precipitate the product, which was suction filtered and air dried. After an overnight drying under high vacuum the yield was 140 mg of a light beige powder. The product structure was characterized by $^1$H NMR, FAB-MS and ICP. $^1$H NMR (DMSO): δ 7.82 (s), 7.02 (d), 6.80 (d), 6.61 (dd), 3.49 (bm), 3.22 (bm), 2.67 (bm). The presence of the broad multiplets in the side chain region indicates that as the site for zinc binding (FIG. 13). FAB-MS: Molecular ion at 1364 and 1366 indicative of bis(triiodothyroninato)zinc with isotopic abundance pattern consistent with zinc. FTIR (neat): $cm^{-1}$ 1582 (C=O stretch); absence of N—H stretch at 1633. Zinc analysis (ICP): Expected 4.8%; Found 4.3%. This supports the structure as shown in FIG. 25 and is about 90% pure, where most of the contamination is probably due to water and may be a hydrate as seen in the $^1$H NMR spectrum.

Preparation of Magnesium Triiodothyronine Complex in the Presence of Water.

Triiodothyronine or T3 (188 mg) was dissolved in 3.5 mL of anhydrous DMSO, after which 0.29 mL of 1 M potassium t-butoxide in t-butanol was added and the solution stirred for 10 minutes. Magnesium chloride (16 mg) in 0.5 mL of water was added and the solution stirred overnight. The solution was poured into 10 mL of deionized water to precipitate the product, which was suction filtered and air dried. After an overnight drying under high vacuum the yield was 188 mg of a light beige powder. The product structure was characterized by $^1$H NMR, FAB-MS and ICP. $^1$H NMR (DMSO): δ 7.81 (bs), 7.02 (bs), 6.81 (bd), 6.59 (dd). The other resonances were hiding behind the solvent and water peaks. The sample formed a cloudy suspension in DMSO. FAB-MS: Molecular ion at 652 indicative of protonated T3 with no bound Mg. FTIR (neat): cm$^{-1}$ 1633 (N—H stretch), 1535 (C=O stretch), 1012 (S=O stretch), 949 (S=O—Mg stretch). The strength of the DMSO related stretches relative to the T3 related stretches indicated a mixture of $(DMSO)_x$Mg cation and T3 anion. Magnesium analysis (ICP): Expected 1.8%; Found 0.96%. Potassium analysis (ICP): Found 0.23%. From the ICP data it appears that this product is a mixture of the magnesium salt, the potassium salt and the zwitterion.

Preparation of Bis(minocyclinato)magnesium

Figure 26:
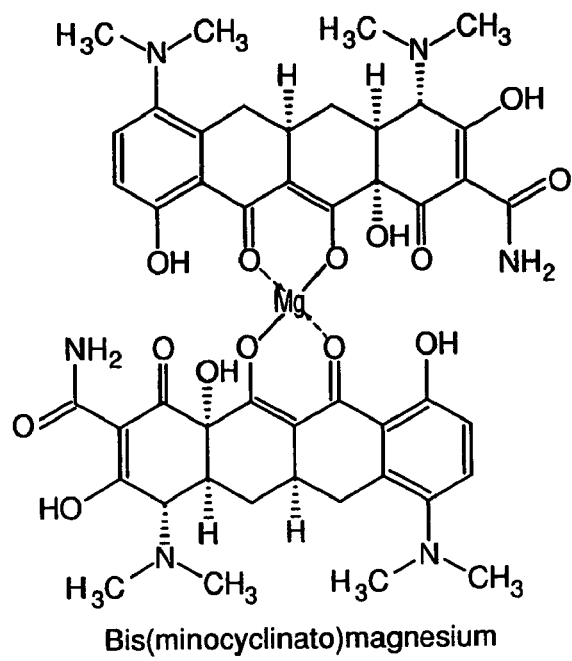
FIG. 26 illustrates the structure of Bis(minocyclinato)magnesium in accordance with the present invention.

Minocycline (104 mg) was dissolved in 3 mL of anhydrous DMSO, after which 0.44 mL of 1 M potassium t-butoxide in t-butanol was added and the solution stirred for 10 minutes. Magnesium chloride (11 mg) was added and the solution stirred overnight. The solution was poured into 10 mL of deionized water to precipitate the product, which was suction filtered and air dried. After an overnight drying under high vacuum the yield was 52 mg of a deep yellow powder. The product structure could not be characterized by $^1$H NMR, possibly due to the different permutations of bidentate complex forms possible with anionic Minocycline and magnesium. The product was characterized, then, by FAB-MS and ICP. FAB-MS: Molecular ion at 937.4 indicative of bis(minocyclinato)magnesium. Magnesium analysis (ICP): Expected 2.68%; Found 2.61%. This confirms that there are two Minocycline molecules per magnesium atom, as represented by a likely structure shown in FIG. 26 (see discussion for Tetracycline below). The product about 97% pure, which most of the contamination is probably due to water as seen in the $^1$H NMR spectrum.

Preparation of Bis(tetracyclinato)magnesium

Figure 27:
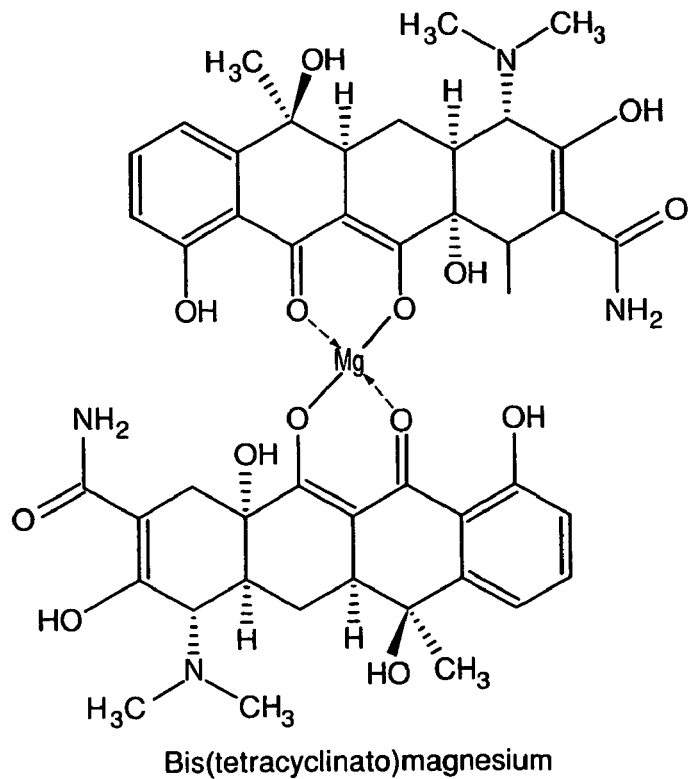
FIG. 27 illustrates the structure of Bis(tetracyclinato)magnesium in accordance with the present invention.

Tetracycline (89 mg) was dissolved in 0.5 mL of anhydrous DMSO, after which 0.2 mL of 1 M potassium t-butoxide in t-butanol was added and the solution stirred for 10 minutes. Magnesium chloride (11 mg) was added and the solution stirred for 3 hours. The solution was concentrated in vacuo at 30° C., after which 0.5 mL of deionized water was added and the mixture triturated and transferred to a 2 mL microcentrifuge tube. The product was separated from the liquid by centrifuging at 8,000 rpm for 6 minutes and the supernatant was decanted. The pellet was washed by adding 0.5 mL of water, vortex mixed, centrifuged and the supernatant decanted. The washing procedure was repeated. After an overnight drying under high vacuum the yield was 72 mg of a deep yellow powder. The $^1$H NMR spectrum (FIG. 20) resembled a polymeric structure, which contained broad multiplets between 8.8 and 10.1 ppm, 6.4 and 7.8 ppm, 4.2 and 5.0 ppm and 1.1 and 3.1 ppm. The product structure could not be accurately characterized by $^1$H NMR, possibly due to the different permutations of bidentate complex forms possible with anionic Tetracycline and magnesium and the moderately slow equilibrium between those isomeric complex forms. Confirmation was observed by adding approximately 1 equivalent of 12 N HCl to the NMR sample and reanalyzing by $^1$H NMR, which revealed reversion of the magnesium complex back to tetracycline and, presumably, magnesium chloride (FIG. 18). The product was further characterized by MALDI-ES and ICP. MALDI-ES: Molecular ion at 911.3 indicative of bis(tetracyclinato)magnesium. Magnesium analysis (ICP): Expected 2.67%; Found 2.53%. FTIR does not indicate presence of a DMSO ligand. This indicates that there are two Tetracycline molecules per magnesium atom. According to NMR evidence from previously published studies of tetracycline-magnesium complexation in aqueous systems, a likely structure for bis(tetracyclinato)magnesium is shown in FIG. 27. The product about 95% pure, which most of the contamination is probably due to solvents as seen in the $^1$H NMR spectrum.

Preparation of Magnesium Tetracycline Complex in Water

Tetracycline (89 mg) was dissolved in 1.5 mL of water, after which 0.2 mL of 1 M potassium t-butoxide in t-butanol was added and the solution stirred for 10 minutes. Magnesium chloride (0.11 mL of 1M solution) was added and the solution stirred for 3 hours. The resultant precipitant was separated from the water by centrifuging at 8,000 rpm for 6 minutes and the supernatant was decanted. The pellet was washed by adding 1 mL of water, vortex mixed, centrifuged and the supernatant decanted. After an overnight drying under high vacuum the yield was 65 mg of a deep yellow powder. The $^1$H NMR spectrum very closely resembled the complex prepared in anhydrous DMSO. Magnesium analysis (ICP): Expected 2.67%; Found 2.42%. It appears that performing the complexation in water versus under anhydrous conditions has a minor impact on the stability and structure of the tetracycline-magnesium complex.

Preparation of Hydrochlorothiazide Zinc Complex

Hydrochlorothiazide (120 mg) was dissolved in 0.5 mL of anhydrous DMSO, after which 0.4 mL of 1 M potassium t-butoxide in t-butanol was added and the solution stirred for 10 minutes. Zinc chloride in diethyl ether (0.2 mL of 1M solution) was added and the solution stirred for 4 hours. The solution was concentrated in vacuo at 30° C., after which 0.5 mL of methanol was added and the mixture triturated and transferred to a 2 mL microcentrifuge tube. The product was separated from the liquid by centrifuging at 8,000 rpm for 6 minutes and the supernatant was decanted. The pellet was washed by adding 0.5 mL of methanol, vortex mixed, centrifuged and the supernatant decanted. The washing procedure was repeated. After an overnight drying under high vacuum the yield was 104 mg of a free flowing white powder. The product was apparently hygroscopic due to the powder turning gummy after a few minutes exposure to ambient air. The $^1$H NMR spectrum resembled a polymeric structure (FIG. 21), which contained broad multiplets between 6.3 and 8.0 ppm, and 4.4 and 5.9 ppm. The product structure could not be accurately characterized by NMR, possibly due to the different permutations of complex forms possible with anionic hydrochlorothiazide and zinc, and the moderately slow equilibrium between those isomeric complex forms. Confirmation was observed by adding approximately 1 equivalent of 12 N HCl to the NMR sample and reanalyzing by $^1$H NMR, which revealed reversion of the zinc complex back to hydrochlorothiazide and, presumably, zinc chloride (FIG. 22). The product was further characterized by MALDI-ES and ICP. MALDI-ES: Molecular ions at 705.9 and 932.9 with typical zinc isotopic abundances but not indicative of any particular hydrochlorothiazide zinc complex structure. Zinc analysis (ICP): Found 10.4%. FTIR (neat): cm$^{-1}$ 1027 (S=O stretch), 953 (S=O—Zn stretch); absence of N—H stretch at 1646.

NMR, MALDI and ICP data clearly indicate the formation of a hydrochlorothiazide-zinc complex. It seems reasonable that the site of complexation may be on one or both of the sulfonamide nitrogens of hydrochlorothiazide. FTIR data suggest the presence of DMSO ligands, which by $^1$H NMR integration the ratio of HCTZ:DMSO is 1:1. Chemical shift of the DMSO methyl groups of 0.08 ppm suggests O-bonding between zinc and DMSO.

Reaction Between Zinc and Hydrochlorothiazide in the Presence of Water

This procedure followed the analogous anhydrous preparation exactly except the zinc chloride was added to 100 μL of water and the ether was allowed to evaporate off prior to adding to the reaction mixture. No product was isolated because the entire mixture slowly dissolved in methanol during the precipitation step. This was putatively due to the formation of methanol soluble hydrated complexes.

Preparation of Dimethylbiguanide Zinc Complex

Figure 28:
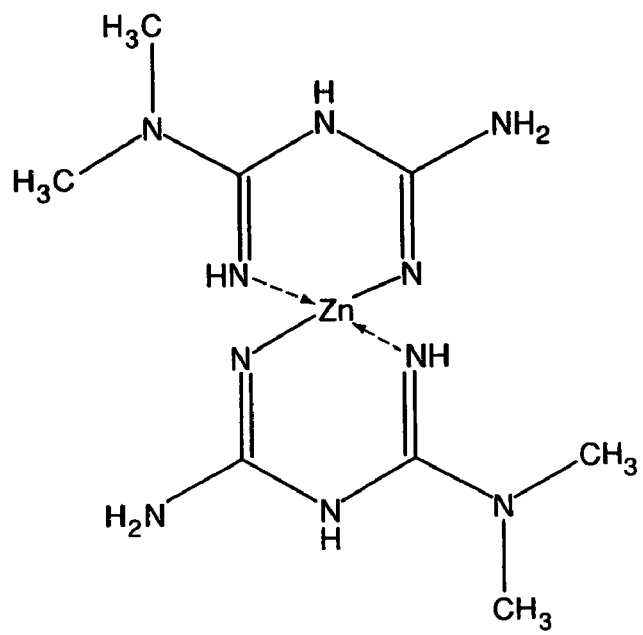
FIG. 28 illustrates the structure of Dimethylbiguanide-zinc complex in accordance with the present invention.

Dimethylbiguanide (66 mg) was dissolved in 1 mL of anhydrous DMSO, after which 0.88 mL of 1 M potassium t-butoxide in t-butanol was added and the solution stirred for 10 minutes. Zinc chloride in diethyl ether (0.22 mL of 1M solution) was added and the solution stirred for 3 hours. The solution was concentrated in vacuo at 35° C., after which 0.5 mL of ethanol was added and the mixture triturated and transferred to a 2 mL microcentrifuge tube. The product was separated from the liquid by centrifuging at 8,000 rpm for 6 minutes and the supernatant was decanted. The pellet was washed by adding 0.5 mL of ethanol, vortex mixed, centrifuged and the supernatant decanted. The washing procedure was repeated. After an overnight drying under high vacuum the yield was 57 mg of a free flowing white powder. $^1$H NMR (DMSO): δ 4.90 (s), 4.66 (s), 4.50 (s), 2.80 (s). The large upfield shifts of —NH protons relative to dimethylbiguanide indicate complexation with zinc. A small upfield shift of 0.05 ppm in the dimethyl groups was also observed in the dimethylbiguanide-zinc complex. FIGS. 14 and 15 show the NMR spectra of dimethylbiguanide-zinc and dimethylbiguanide, respectively. The product was further characterized by ICP. Zinc analysis (ICP): Found 8.14%. FTIR data did not indicate presence of a DMSO ligand. NMR and ICP data clearly indicate the formation of a dimethylbiguanide-zinc complex. FIG. 28 represents the biguanide-metal complex prepared. MALDI-ES analysis did not reveal a zinc containing compound.

Preparation of Zinc Dimethylbiguanide Complex in the Presence of Water

This procedure followed the analogous anhydrous preparation exactly except the zinc chloride was added to 100 μL of water and the ether was allowed to evaporate prior to adding to the reaction mixture. Work up and drying was followed in the same manner to yield 47 mg of a free flowing white powder. The compound was sparingly soluble in DMSO resulting in low signal to noise ratio in the NMR. $^1$H NMR (DMSO): δ 4.90 (bs), 4.66 (bs), 4.50 (bs), 2.85 (s), 2.80 (s). The singlet at 2.85 ppm indicates the presence of dimethylbiguanide that is not complexed with zinc. Judging from the integration of the two peaks at 2.85 and 2.80 ppm, the ratio of free dimethylbiguanide to the zinc complex is about 1:1.

Preparation of Zinc Dimethylbiguanide Complex in Water

Dimethylbiguanide (33 mg) was dissolved in 1 mL of water, after which 0.44 mL of 1 M potassium t-butoxide in t-butanol was added and the solution stirred for 10 minutes. Zinc chloride in diethyl ether (0.22 mL of 1M solution) was added and the solution stirred for 5 hours. The resultant precipitant was separated from the liquid by centrifuging at 8,000 rpm for 6 minutes and the supernatant was decanted. The pellet was washed by adding 1 mL of water, vortex mixed, centrifuged and the supernatant decanted. After an overnight drying under high vacuum the yield was 20 mg of a free flowing white powder which contained no organic material by $^1$H NMR. The isolated product was zinc salts in various hydrated forms.

Preparation of Bis(acycloguanosinato)magnesium

Figure 29:
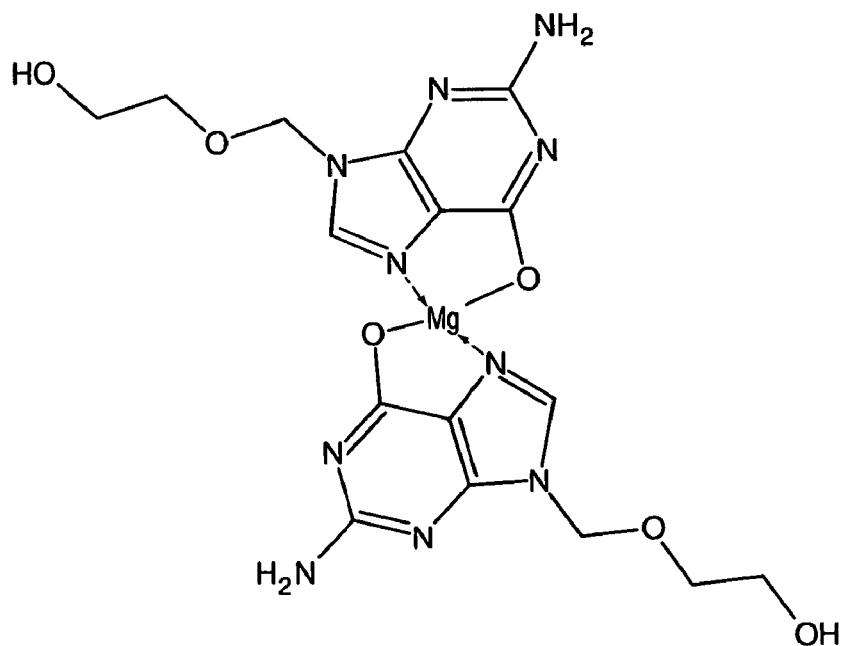
FIG. 29 illustrates the structure of Bis(acycloguanosinato) magnesium in accordance with the present invention.

Acycloguanosine (45 mg) was dissolved in 0.5 mL of anhydrous DMSO, after which 0.2 mL of 1 M potassium t-butoxide in t-butanol was added and the solution stirred for 10 minutes. Magnesium chloride (11 mg) was added and the solution stirred for 4 hours. The solution was concentrated in vacuo at 30° C., after which 0.5 mL of methanol was added and the mixture triturated and transferred to a 2 mL microcentrifuge tube. The product was separated from the liquid by centrifuging at 8,000 rpm for 6 minutes and the supernatant was decanted. The pellet was washed by adding 0.5 mL of methanol, vortex mixed, centrifuged and the supernatant decanted. The washing procedure was repeated. After an overnight drying under high vacuum the yield was 15 mg of a beige coarse powder. The product structure was characterized by $^1$H NMR, MALDI-ES and ICP. $^1$H NMR (DMSO): δ 7.70 (s), 6.75 (bs), 5.30 (s), 4.64 (bs), 3.42 (s). MALDI-ES: Molecular ion at 473.1 is suggestive of bis(acycloguanosine) magnesium. Other molecular ions at 666, 702, 893 and 1065 have not been assigned to a particular structure. Magnesium analysis (ICP): Expected 5.14%; Found 4.16%. FTIR data did not indicate presence of a DMSO ligand. From a combination of the absence of the amide proton at 10.6 ppm, the ICP analysis and the MALDI-ES analysis, the structure for bis (acycloguanosinato)magnesium is shown in FIG. 29.

Partition Coefficients, Distribution Coefficients and $pK_a$ for T3 and Tetracycline Complexes and Reference Drugs Determination of $pK_a$ and log P was done by potentiometry and spectrophotometry. The potentiometric method includes the use of expert software to calculate $pK_a$ and log P from simple acid and base titrations of the analytes. The $pK_a$ was first determined by weighing approximately 2 mg of pure substance into an assay vial. Ionic strength was adjusted with 0.15M KCl and water was added to dissolve the compound followed by an acid or base titrant to drop or raise the pH to the desired starting value. The solution was then titrated with acid (0.5N HCl) or base (0.5N NaOH) to the final pH. Approximate pKa values were displayed and later refined to exact data.

For $(T3)_2Zn$, which is sparingly soluble in water, the pKa was determined in mixtures of water and DMSO cosolvent. A minimum of three ratios of water/DMSO was titrated to obtain $p_sK_a$ (apparent $pK_a$ in the presence of cosolvent). The aqueous $pK_a$ was determined by extrapolation using the Yasuda-Shedlovsky technique.

The log P was determined by a titration in the presence of octanol (water saturated). The $pK_a$ in water and the apparent $pK_a$ in the presence of octanol ($p_oK_a$) were compared and the log P determined. Ton-pairing (partitioning of a charged species into octanol, termed log $P^+$ or log $P^-$) were determined with an additional titration in the presence of another volume of octanol. Using experimentally determined $pK_a$ and log P, a drug lipophilicity profile (log D vs. pH) was calculated. The log $D_{7.4}$ was determined from this profile at pH 7.4.

The spectrophotometric method used a fiber optics dip probe, a UV light source (pulsed deuterium lamp) and a photodiode array detector to automatically capture the absorption spectra of the sample solution in the course of adding an acid or base solution.

Up to a 10 mM stock solution was prepared by dissolving several 0.5 mg samples in 0.5-1.0 mL of water or cosolvent.

An adequate amount of stock is pipetted into the vial for titration. The dip probe is in the assay vial and aqueous 0.15 M KCl solution is added to cover the dip probe. Acid or base is added to bring the pH to the desired starting value. Over the chosen pH range, the spectra changes due to ionization were captured by the photodiode array detector for subsequent analysis. Target Factor Analysis (TFA) was applied to deduce the $pK_a$ values of the sample and resolve the major absorptivity spectra of the reducing species. The aqueous $pK_a$ was determined by extrapolation using the Yasuda-Shedlovsky technique. The $pK_a$ values obtained from spectrophotometric experiments are in excellent agreement with those derived from potentiometric titrations.

Bioavailability Study

Title: Assessment of absorbance and effect of a hormone complex supplementation in Sprague Dawley rats Test subjects: Fifteen young female Sprague Dawley rats (180-225 gms) were used. These rats were obtained from a commercial source (Harlan Laboratory Animals, Dublin, Va.), housed in the Vivarium at Litton Reeves Hall (Division of Laboratory Animal Resources), in groups of three in polypropylene shoebox cages. Water was available ad libitum. Rats were fed certified rodent chow ad libitum. After arrival, the health of rats were assessed and animals were placed in quarantine for a minimum of five days, during which time, general health was assessed. At the end of quarantine, rats were moved to permanent animal quarters for access and study.

Study design: This is a study to compare the absorption and effect of three hormones administered to rats orally directly into the esophagus. T3-Zinc and T3-Magnesium were synthesized, which are the two test compounds. Triiodothyronine, free acid (T3) was the positive control. The three compounds were formulated, separately, into gelatin capsules, with a total dose of 108±12 µg/kg administered. In order to avoid acid degradation of the test compounds in the rat stomach, metal oxides were added to the formulation—to the T3-magnesium compounds, 1.08±0.13 mg of magnesium oxide was added and to the T3-zinc compounds, 106±13 µg of zinc oxide was added. Another T3 control was included, where 145±50 µg of zinc oxide was added to T3, free acid.

For dosing and blood collection, three rats per replicate were anesthetized. A baseline blood sample was collected, by retroorbital sampling. Then, compound was administered orally by gavage tube. Following administration, blood samples (500 µL) were collected at 0.5, 1, 2, 2.5, 5 hours after dosing. Blood samples were centrifuged, the sera removed and the sera kept on ice and then analyzed for serum triiodothyronine levels.

Analysis of samples: Serum triiodothyronine levels were determined by RIA.

Figure 30:
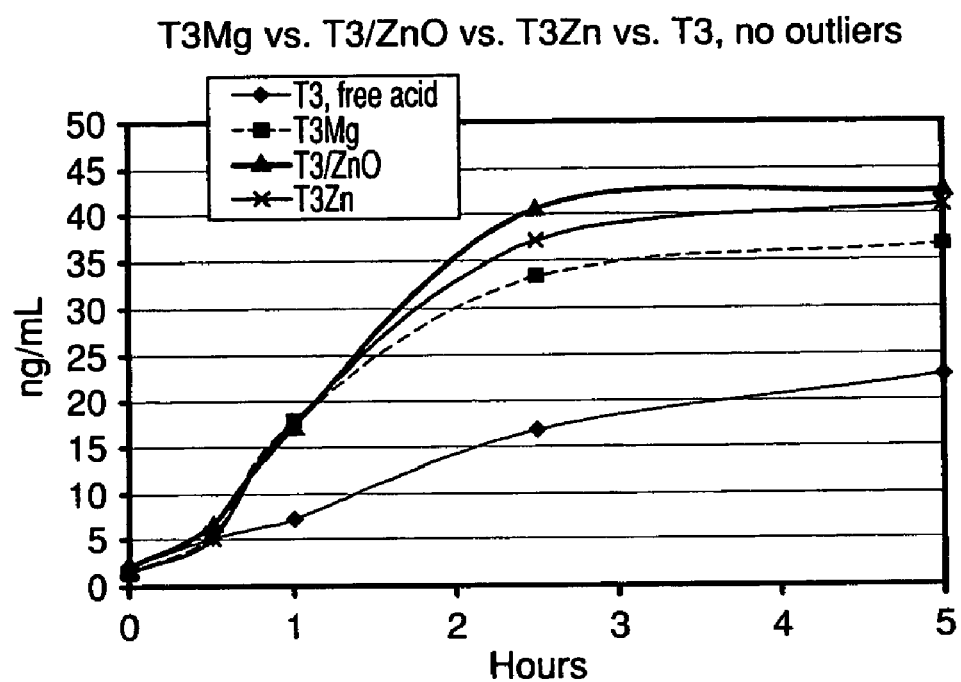
FIG. 30 illustrates the relative pharmacokinetic profile of T3, T3Mg, T3Zn in a rat animal model in accordance with the present invention.

Results: The individual serum T3 levels from each group of rats were averaged and a plot of T3 concentration (ng/mL) vs. hour was produced. The plot is shown in FIG. 30.

Large Molecule Example:

Preparation of Interference RNA

Interference RNA was prepared using a modified New England Biolabs Litmus 28i RNAi bidirectional transcription vector. A 922 bp bovine serum albumin cDNA fragment was introduced into the Bgl II and StuI sites of the Litmus RNAi vector. The target RNAi transcript was produced by in vitro transcription with T7 RNA Polymerase to yield 1 mg/ml. The RNA was then divided into 50 ug samples and freeze dried Preparation of RNA:Magnesium Inner Coordination (Covalent) Complex Approximately 50 µg of iRNA was dissolved in 100 µL of anhydrous DMSO at 50° C. A stock solution of 4 mM magnesium chloride was prepared by dissolving 19 mg of anhydrous magnesium chloride in anhydrous DMSO. Three separate reactions were run where 15 µL, 30 µL and 60 µL of 4 mM magnesium chloride was added to three separate solutions of iRNA in DMSO. The solutions were allowed to set at room temperature with occasional vortex mixing for 90 minutes at which time 20 µL of 7.5 M aqueous ammonium chloride followed by 400 µL of RNAse free ethanol was added and vortex mixed. The product was allowed to precipitate out of solution over 1 hour, centrifuged and the liquid decanted from the pellet. The pellet was washed with 100 µL of RNAse free ethanol, vortex mixed, centrifuged and the ethanol supernatant decanted off the pellet. The resultant colorless pellet was air-dried for several minutes before testing in the isoelectric focusing gel.

Preparation of Magnesium:RNA Outer Coordination (Ionic) Complex

The preparation for the ionic magnesium:RNA complex followed the procedure for the covalent analog exactly except the stock magnesium chloride solution was prepared in RNAse free water instead of anhydrous DMSO. The resultant colorless pellet was air-dried for several minutes before testing in the isoelectric focusing gel.

Preparation of RNA:Zinc Inner Coordination (Covalent) Complex

The preparation for the covalent zinc:RNA complex followed the procedure for the magnesium analog exactly except a stock zinc chloride solution was prepared instead of a stock magnesium chloride solution. The resultant colorless pellet was air-dried for several minutes before testing in the isoelectric focusing gel.

Preparation of Zinc:RNA Outer Coordination (Ionic) Complex

The preparation for the ionic zinc:RNA complex followed the procedure for the covalent analog exactly except the stock zinc chloride solution was prepared in RNAse free water instead of anhydrous DMSO. The resultant colorless pellet was air-dried for several minutes before testing in the isoelectric focusing gel.

Isoelectric Focusing Gel Experiment

This is a novel approach of using IEF gels to monitor for the anticipated modification of the iRNA target. FIG. 31 shows the results from the initial experiment.

Interpretation of IEF Experiments

The IEF experiment showed that magnesium RNA complexes prepared in anhydrous (A) conditions with three concentrations of magnesium chloride produced covalent complexes in approximately 50% yield. Magnesium RNA complexes prepared in aqueous (W) conditions with three concentrations of magnesium chloride produced ionic complexes. The zinc RNA complex prepared in anhydrous (A) conditions with zinc chloride produced a covalent complex in approximately 50% yield. The zinc RNA complex prepared in aqueous (W) conditions with zinc chloride produced an ionic complex.

The invention claimed is:

1. A metal coordination complex of a biologically active moiety and a metal, wherein:
    the biologically active moiety is selected from the group consisting of Zanamivir, Montelukast, Epoetin, Methotrexate, Hydralazine, Carbergoline, Gentamycin, Tobramycin, Acarbose, interference ribonucleic acid (iRNA), Atorvastatin, Lansoprazole, Losartan, Olanzapine, Gabapentin, Pemetrexed, Tenofovir, and derivatives thereof; and wherein the metal is selected from the group consisting of aluminum, bismuth, calcium, copper, iron, magnesium, silicon, and zinc;

provided that the complex does not include a lansoprazole-Cu (II)-eosin.

2. The complex of claim 1 wherein the biologically active moiety is selected from the group consisting of Zanamivir, Montelukast, Epoetin, Methotrexate, Hydralazine, Carbergoline, Gentamycin, Tobramycin, Acarbose, and derivatives thereof.

3. The complex of claim 1 wherein the biologically active moiety is selected from the group consisting of iRNA, Atorvastatin, Lansoprazole, Losartan, Olanzapine, Gabapentin, Pemetrexed, and derivatives thereof.

4. The complex of claim 1 wherein the biologically active moiety is Tenofovir and derivatives thereof.

5. The complex of claim 1 wherein the biologically active moiety is selected from the group consisting of antidiabetics, antiGERDs, antineoplastics, antivirals, antihypertensives, antibiotics, antiparkinsonians, hormone replacements, diuretics, antipsoriatics, antirheumatics, antiepileptics, antidepressants, and analgesics.

6. The complex of claim 1 wherein the biologically active moiety comprises a guanide functionality, a diamine functionality or a combination thereof.

7. The complex of claim 1 wherein the biologically active moiety comprises Lansoprazole.

8. The complex of claim 7 wherein the metal is selected from the group consisting of calcium, copper, magnesium, and zinc.

9. The complex of claim 8 wherein the metal is magnesium.

10. A method of modulating properties of a biologically active moiety comprising:

forming a metal coordination complex of the biologically active moiety with a metal;

wherein the biologically active moiety is selected from the group consisting of Zanamivir, Montelukast, Epoetin, Methotrexate, Hydralazine, Carbergoline, Gentamycin, Tobramycin, Acarbose, iRNA, Atorvastatin, Lansoprazole, Losartan, Olanzapine, Gabapentin, Pemetrexed, Tenofovir, and derivatives thereof; and wherein the metal is selected from the group consisting of aluminum, bismuth, calcium, copper, iron, magnesium, silicon, and zinc;

provided that the complex does not include a lansoprazole-Cu (II)-eosin.

11. The method of claim 10 wherein the biologically active moiety is selected from the group consisting of Zanamivir, Montelukast, Epoetin, Methotrexate, Hydralazine, Carbergoline, Gentamycin, Tobramycin, Acarbose, and derivatives thereof.

12. The method of claim 10 wherein the biologically active moiety is selected from the group consisting of iRNA, Atorvastatin, Lansoprazole, Losartan, Olanzapine, Gabapentin, Pemetrexed, and derivatives thereof.

13. The method of claim 10 wherein the biologically active moiety is Tenofovir and derivatives thereof.

14. The method of claim 10 wherein the biologically active moiety is selected from the group consisting of antidiabetics, antiGERDs, antineoplastics, antivirals, antihypertensives, antibiotics, antiparkinsonians, hormone replacements, diuretics, antipsoriatics, antirheumatics, antiepileptics, antidepressants, and analgesics.

15. The method of claim 10 wherein the biologically active moiety comprises a guanide functionality, a diamine functionality or a combination thereof.

16. The method of claim 10 wherein the biologically active moiety comprises Lansoprazole.

17. The method of claim 16 wherein the metal is selected from the group consisting of bismuth, copper, magnesium, and zinc.

18. The method of claim 16 wherein the metal is magnesium.

19. The method of claim 10 wherein the properties to be modulated are selected from the group consisting of: dissolution rate, solubility, potency, stability, absorbability, targeted delivery, and combinations thereof.

20. A metal coordination complex of a biologically active moiety and a metal, wherein:

the biologically active moiety is selected from the group consisting of Zanamivir, Montelukast, Epoetin, Methotrexate, Hydralazine, Carbergoline, Gentamycin, Tobramycin, Acarbose, and derivatives thereof; and wherein the metal is selected from the group consisting of aluminum, bismuth, calcium, copper, iron, magnesium, silicon, and zinc.

21. The complex of claim 20 wherein the biologically active moiety is selected from the group consisting of Zanamivir and Montelukast.

22. The complex of claim 21 wherein the biologically active moiety comprises Zanamivir.

23. The method of claim 10 wherein the metal is calcium.

24. The complex of claim 1 wherein the metal is calcium.

25. The complex of claim 7 wherein the metal is calcium.

26. A metal coordination complex of a biologically active moiety and a metal, wherein:

the biologically active moiety is selected from the group consisting of: Enalapri, Ramipril, and derivatives thereof; and wherein the metal is selected from the group consisting of: aluminum, bismuth, calcium, iron, magnesium, silicon, and zinc.

27. A method of modulating properties of a biologically active moiety comprising:

forming a metal coordination complex of the biologically active moiety with a metal;

wherein the biologically active moiety is selected from the group consisting of: Enalapri, Ramipril, and derivatives thereof; and wherein the metal is selected from the group consisting of: aluminum, bismuth, calcium, iron, magnesium, silicon, and zinc.

28. A metal coordination complex of a biologically active moiety and a metal, wherein:

the biologically active moiety is selected from the group consisting of: Metronidazole and derivatives thereof; and wherein the metal is selected from the group consisting of: aluminum, bismuth, calcium, iron, magnesium, and silicon.

29. A method of modulating properties of a biologically active moiety comprising:

forming a metal coordination complex of the biologically active moiety with a metal;

wherein the biologically active moiety is selected from the group consisting of: Metronidazole and derivatives thereof; and wherein the metal is selected from the group consisting of: aluminum, bismuth, calcium, iron, magnesium, and silicon.

* * * * *